United States Patent [19]

Minai et al.

[11] Patent Number: 5,191,109

[45] Date of Patent: Mar. 2, 1993

[54] PROCESS FOR PREPARING OPTICALLY ACTIVE CYCLOPENTENONES

[75] Inventors: Masayoshi Minai, Moriyama; Sachiko Imazu, Minoo; Seiichi Kai, Nara; Takaharu Ikeda, Ibaraki; Hideyuki Ikehira, Osaka, all of Japan

[73] Assignee: Sumitomo Chemical Company, Limited, Osaka, Japan

[21] Appl. No.: 648,893

[22] Filed: Jan. 31, 1991

[30] Foreign Application Priority Data

Feb. 2, 1990 [JP] Japan .................................. 2-24738
Feb. 2, 1990 [JP] Japan .................................. 2-24739
Feb. 2, 1990 [JP] Japan .................................. 2-24740
Jul. 13, 1990 [JP] Japan .................................. 2-185930
Jul. 18, 1990 [JP] Japan .................................. 2-191347

[51] Int. Cl.$^5$ ............................................. C07C 69/74
[52] U.S. Cl. .................................. 560/121; 560/190; 549/501; 435/135
[58] Field of Search ................. 435/280, 136, 135; 560/190, 121; 562/595

[56] References Cited

U.S. PATENT DOCUMENTS

| 4,271,314 | 6/1981 | Collins et al. . |
| 4,322,543 | 3/1982 | Collins et al. . |
| 4,812,585 | 3/1989 | Kondo et al. . |
| 4,952,710 | 8/1990 | Babiak et al. . |
| 4,957,867 | 9/1990 | Minai et al. . |

FOREIGN PATENT DOCUMENTS

| 0357009 | 3/1990 | European Pat. Off. . |
| 0362816 | 4/1990 | European Pat. Off. . |
| 2758882 | 7/1979 | Fed. Rep. of Germany . |

OTHER PUBLICATIONS

Collins et al, J. Med. Chem., 1983, 26, 786–790.
Abstract J6319867-A, 1988.
Abstract J64–46, 1989.
Abstract J 61081797A, 1986.
Abstract J 61092578-A, 1986.
Abstract J 63109797-A, 1988.
Abstract J01108989-A, 1989.
Abstract J 63077837-A, 1988.
Abstract J 62–42-A, 1987.
L. Miller et al, Journal of Chromatography, vol. 511, pp. 97–107, 1990.
Klünenberg et al, Angewandte Chemia, Internatl. Edition, vol. 17, pp. 47–48, No. 1 (1978).
Journal of Medicinal Chemistry, vol. 26, No. 6, pp. 786–790, (Jun. 1983) Collins et al.
J. S. Ng et al; Tetrahedron Letters, vol. 29, No. 25, pp. 3045–3048, (1988).

Primary Examiner—Michael L. Shippen
Attorney, Agent, or Firm—Birch, Stewart, Kolasch & Birch

[57] ABSTRACT

An improved process for preparing an optically active 4-hydroxycyclopentenone of the formula:

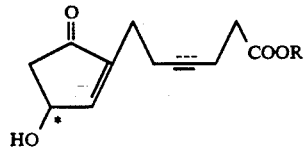

[I]

wherein R is a lower alkyl, the symbol ≡ means double bond or triple bond, and the * marked carbon is an asymmetric carbon, and the corresponding racemic 4-hydroxycyclopentenone, which are useful as an intermediate for preparing medicinal or agricultural products, particularly pharmaceutically active prostaglandins, and intermediates for preparing the optically active and/or racemic 4-hydroxycyclopentenone.

11 Claims, No Drawings

PROCESS FOR PREPARING OPTICALLY ACTIVE CYCLOPENTENONES

TECHNICAL FIELD

This invention relates to an improved process for preparing optically active cyclopentenones which are useful as an intermediate for preparing medical or agricultural products, particularly pharmaceutically active prostaglandins. More particularly, it relates to optically active 4-hydroxycyclopentenones of the formula:

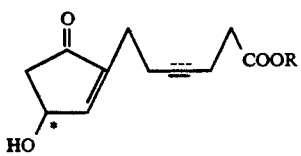

wherein R is a $C_1$–$C_6$ alkyl, the symbol ≡ means double bond or triple bond, and the * marked carbon is an asymmetric carbon.

PRIOR ART

It is known that the racemic 4-hydroxycyclopentenones of the above formula [I] are useful as an intermediate for preparing prostaglandins (cf. J. Med. Chem., Vol. 26, 786, 1983), wherein the 4-hydroxycyclopentenones are prepared by a process as shown in the following reaction scheme.

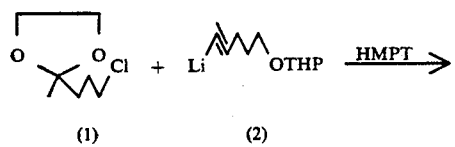

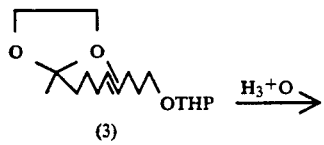

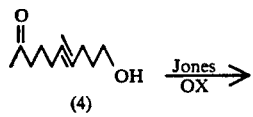

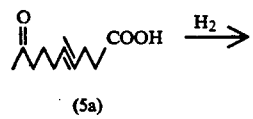

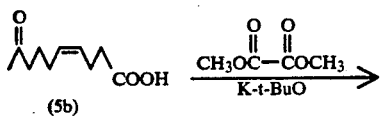

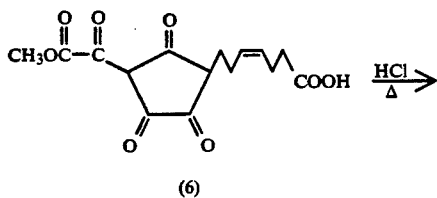

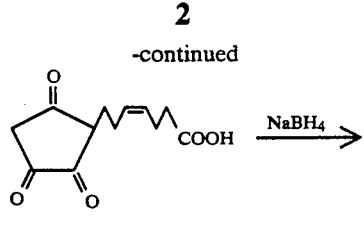

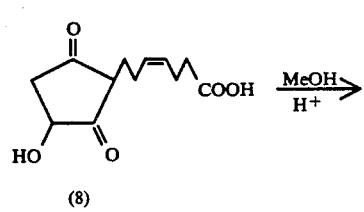

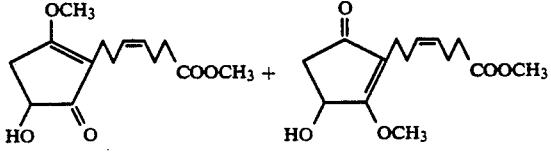

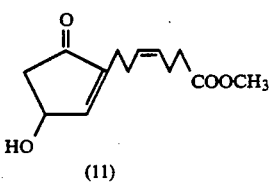

However, the above process is not advantageous for industrial production of the 4-hydroxycyclopentenones because it requires many reaction steps and the sub-materials are very expensive and further the products are only obtained in a racemic mixture.

On the other hand, it is also known that acetylenedicarboxylic acids of the formula:

wherein R is a $C_1$–$C_6$ alkyl, are prepared by the following two processes.

(1) A process by a reaction utilizing metathesis as shown in the following reaction scheme (cf. Tetrahedron Letters, 23 (49), 5139–5140, 1982):

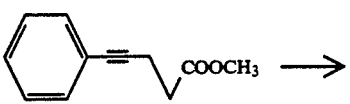

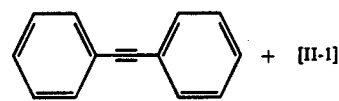

(2) A process utilizing malonic acid diesters as shown in the following reaction scheme (cf. Journal of Chemical Society, 3208, 1954):

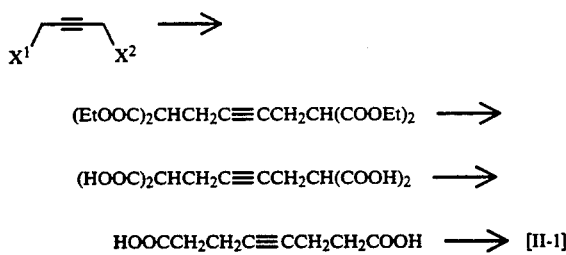

However, these processes are still not satisfactory for the industrial production of the products because in the process (1) the starting material is hardly obtainable and the process (2) requires too many steps.

SUMMARY OF THE INVENTION

An object of this invention is to provide an improved process for preparing optically active 4-hydroxycyclopentenones which can give the desired product on industrial scale. Another object of the invention is to provide a process for preparing the racemic 4-hydroxycyclopentenones on industrial scale. A further object of the invention is to provide intermediates for the 4-hydroxycyclopentenones and processes for preparing the same. These and other objects and advantages of this invention will be apparent to those skilled in the art from the following description.

DETAILED DESCRIPTION OF THE INVENTION

The improved process for preparing the desired optically active 4-hydroxycyclopentenones [I] of this invention is illustrated by the following reaction scheme:

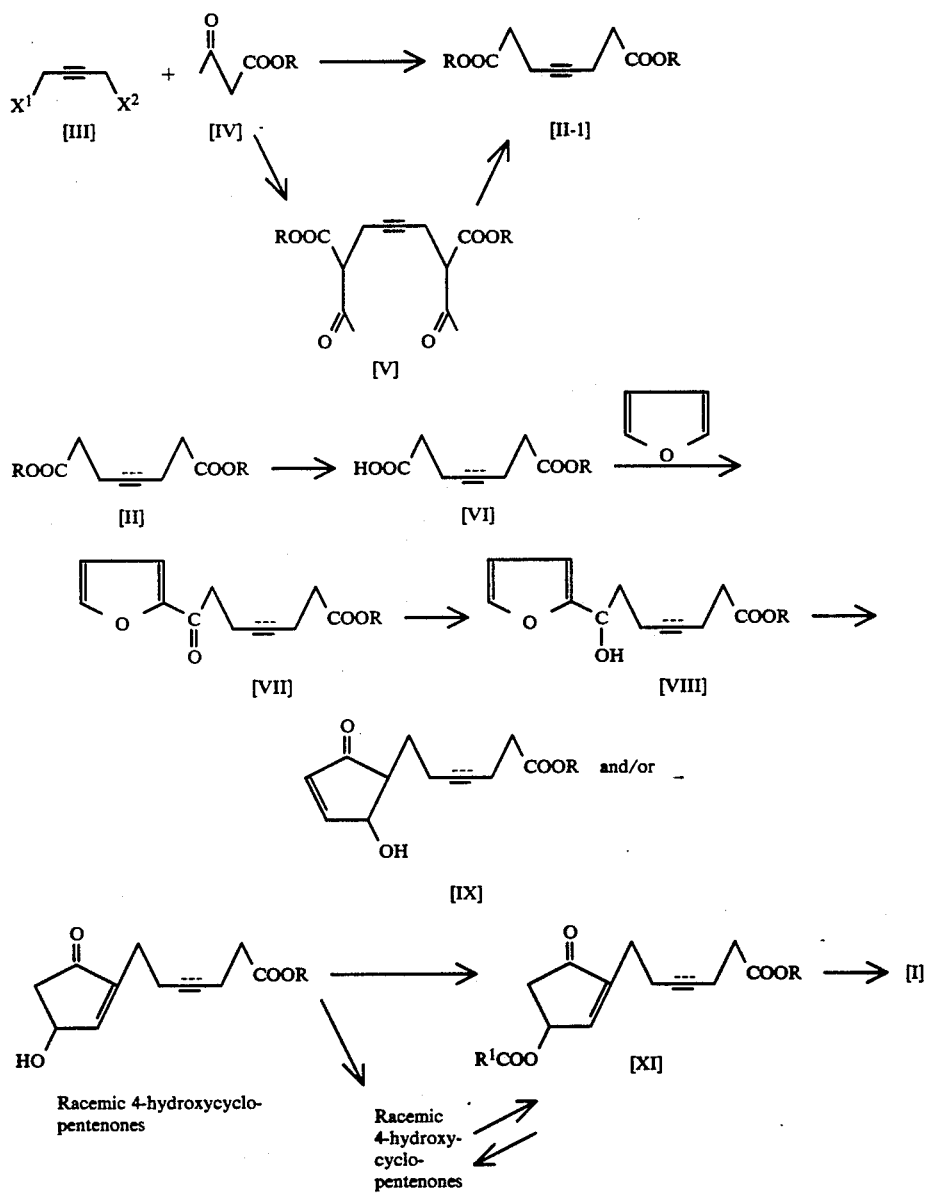

In the above reaction scheme, R and the symbol $\equiv$ are as define above, and $R^1$ is a $C_1$–$C_5$ alkyl having optionally a halogen substituent, $X^1$ and $X^2$ are each chlorine atom, bromine atom, iodine atom, methanesulfonyloxy, or p-toluenesulfonyloxy.

Along with the above reaction scheme, the process of this invention is explained in detail below.

The desired optically active 4-hydroxycyclopentenones [I] are prepared by asymmetrically hydrolyzing cyclopentenone esters of the formula [XI] with an esterase which can preferentially hydrolyze either one of the optically active forms of the cyclopentenone esters.

The esterase used therein is in broad sense including lipase.

The esterase can be produced by various microorganisms being capable of producing an esterase which can asymmetrically hydrolyze the cyclopentenone esters [XI].

The microorganisms include, for example, those of the genera Enterobacter, Arthrobacter, Brevibacterium, Pseudomonas, Alcaligenes, Micrococcus, Chromobacterium, Microbacterium, Corynebacterium, Bacillus, Lactobacterium, Trichoderma, Candida, Saccharomyces, Rhodotorula, Cryptococcus, Torulopsis, Pychia, Penicillium, Aspergillus, Rhizopus, Mucor, Aureovacidium, Actynomucor, Nocardia, Streptomyces, Hansenula, and Achromobacter.

The cultivation of these microorganisms can be carried out in a conventional manner, for example, in a liquid medium.

For example, a microrganism is inoculated in a sterilized liquid medium [e.g. a maltose extract-yeast extract medium (which is prepared by dissolving peptone (5 g), glucose (10 g), malt extract (3 g) and yeast extract (3 g) in water (1 liter) and adjusting to pH 6.5) for cultivation of fungi, yeast; a saccharide-added bouillon medium (which is prepared by dissolving glucose (10 g), peptone (5 g), meat extract (5 g) and NaCl (3 g) in water (1 liter) and adjusting to pH 7.2) for cultivation of bacteria], and is cultivated at 20° to 40° C. for 1 to 3 days by shake culture, optionally by solid culture.

Some esterases derived from microorganisms are commercially available, for example, lipase derived from Pseudomonas (Lipase P, manufactured by Amano Seiyaku K.K., Japan), lipase derived from Aspergillus (Lipase AP, manufactured by Amano Seiyaku K.K.), lipase derived from Mucor (Lipase M-AP, manufactured by Amano Seiyaku K.K.), Lipase derived from *Candida cylindrase* (Lipase MY, manufactured by Meito Sangyo K.K., Japan), lipase derived from Alcaligenes (Lipase PL, manufactured by Meito Sangyo K.K.), lipase derived from Achromobacter (Lipase AL, manufactured by Meito Sangyo K.K.), lipase derived from Arthrobacter (Lipase GODO BSL, manufactured by Godo Shusei K.K., Japan), lipase derived from Chromobacterium (manufactured by Toyo Jozo Co., Ltd., Japan), lipase derived from *Rhizopus delemar* (Talipase, manufactured by Tanabe Seiyaku Co., Ltd., Japan), and lipase derived from Rhizopus (Lipase Saiken, manufactured by Osaka Bacterial Institute, Japan).

Esterases derived from animals and vegetables can also be used. Samples thereof are steapsin, pancreatin, pig liver esterase, and wheat germ esterase.

The esterases derived from microorganisms, animals or vegetables can be used in various forms such as purified enzyme, crude enzyme, enzyme-containing substance, culture broth, culture or cells of microorganisms, filtrate of the culture broth, or physically treated products of these substances, or combination of enzyme and microorganism. Alternatively, these enzymes or cells of microorganisms may be in the form of being immobilized on a substrate such as resins.

The asymmetrical hydrolysis is usually carried out by virgorously stirring a mixture of the starting cyclopentenone ester [XI] and an esterase (e.g. an enzyme, a microorganism, or a mixture thereof) in a buffer.

The buffer includes any conventional buffers, for example, inorganic acid salt buffers (e.g. sodium phosphate buffer, potassium phosphate buffer, etc.), and organic acid salt buffers (e.g. sodium acetate buffer, sodium citrate buffer, etc.), which have a pH in the range of 8 to 11 in case of culture broth of alkali-philic microorganisms or alkaline esterase; in the range of 5 to 8 in case of culture broth of microorganism other than alkali-philic ones or esterase having no alkali resistance. The buffer has usually a concentration of 0.05 to 2 M, preferably 0.05 to 0.5 M.

The asymmetric hydrolysis is usually carried out at a temperature of 10° to 60° C. for 10 to 70 hours, but is not limited to these conditions.

When the asymmetric hydrolysis is carried out by using a lipase derived from Pseudomonas or Arthrobacter, the obtained 4-hydroxycyclopentenones (I) have comparatively higher optical purity.

In the asymmetric hydrolysis, there may be used an inert solvent such as toluene, chloroform, methyl isobutyl ketone, dichloromethane, etc. in addition to the buffer, by which the asymmetric hydrolysis proceeds advantageously.

By the above asymmetric hydrolysis, either one of optically active forms of the cyclopentenone esters [XI] is selectively hydrolyzed to give the desired optically active 4-hydroxycyclopentenones [I], wherein another optically active form of the cyclopentenone esters [XI] is retained in the reaction system without being hydrolyzed.

After the hydrolysis is completed, the desired optically active 4-hydroxycyclopentenones [I] are isolated and separated from the remaining other cyclopentenone ester by the steps of extracting the reaction mixture with a solvent (e.g. methyl isobutyl ketone, ethyl acetate, diethyl ether, etc.), distilling the extract to remove the solvent, and subjecting to a conventional purification, such as column chromatography.

The other optically active form of cyclopentenone esters obtained by the above procedure without being hydrolyzed may optionally be further hydrolyzed to convert it into 4-hydroxycyclopentenones which are an enantiomorph of the above-isolated optically active 4-hydroxycyclopentenones (I).

The desired optically active 4-hydroxycyclopentenones [I] can be prepared by the above processes and the products thus prepared may optionally be purified by a conventional method such as column chromatography.

The cyclopetenone esters [XI] can be prepared by esterifying the racemic 4-hydroxycyclopentenones with a carboxylic acid of the formula [X]:

   [X]

wherein $R_1$ is a $C_1$–$C_5$ alkyl having optionally a halogen substituent, or a derivative thereof.

The carboxylic acid [X] or derivative thereof used as an esterifying agent in the esterification reaction includes lower alkylcarboxylic acid anhydrides or halides, such as acetic anhydride, propionic anhydride, acetyl chloride, acetyl bromide, propionyl chloride, propionyl bromide, butyryl chloride, butyryl bromide, valeryl chloride, valeryl bromide, and the like; and halogen-substituted lower alkylcarboxylic acids or derivatives, such as chloroacetic acid, chloroacetyl chloride, chloroacetyl bromide, chloroacetic anhydride, chloropropionic acid, chloropropionyl chloride, chloropropionyl bromide, chloropropionic anhydride, and the like.

The reaction of the racemic 4-hydroxycyclopentenones and the carboxylic acid [X] or derivative thereof is usually carried out in an appropriate solvent or without solvent in the presence of a basic substance or an acid substance.

The solvent used therein includes conventional aliphatic or aromatic inert solvents, for example, ethers (e.g. tetrahydrofuran, diethyl ether, etc.), ketones (e.g. acetone, methyl ethyl ketone, etc.), aromatic hydrocarbons (e.g. toluene, benzene, etc.), aliphatic hydrocarbons (e.g. hexane, etc.), organic amines (e.g. pyridine, etc.), halogenated aliphatic or aromatic hydrocarbons (e.g. chlorobenzene, dichloromethane, dichloroethane, chloroform, carbon tetrachloride, etc.), aprotic polar solvents (e.g. dimethylformamide, etc.), or a mixture of two or more thereof. The amount of the solvent is not critical.

The amount of the carboxylic acid [X] or derivative thereof is not specified but is usually in the range of 1 to 4 equivalents to the racemic 4-hydroxycyclopentenones.

The basic substance used in the above reaction includes organic or inorganic basic compounds, such as dimethylaminopyridine, triethylamine, tri-n-butylamine, pyridine, pycoline, imidazole, sodium carbonate, sodium methylate, potassium hydrogen carbonate, and the like. Instead of the basic substance, there may be used an acid, such as toluenesulfonic acid, methanesulfonic acid, sulfuric acid, and the like. The amount of the basic substance or acid substance may vary depending on the kinds and amounts of the carboxylic acid [X] or derivative thereof or the kinds of the combination of the carboxylic acid or derivative thereof with the basic or acid substance, but in case of using an acid halide as the carboxylic acid or derivative thereof, it is usually used in an amount of one equivalent or more to the acid halide.

The reaction is usually carried out at a temperature of −30° to 100° C., preferably −20° to 90° C. The reaction period is not critical, but when the starting racemic 4-hydroxycyclopentenones are consumed and disappear from the reaction system, the reaction is deemed to be completed.

After the reaction is completed, the desired cyclopentenone esters [XI] are isolated in high yield from the reaction mixture by a conventional method, such as extraction, liquid separation, concentration, recrystallization, and the like. The product may be purified by a conventional method such as column chromatography, but unpurified product may be used for the subsequent step.

The cyclopentenone esters [XI] can alternatively be prepared by reacting the 3-hydroxycyclopentenones [IX] and/or racemic 4-hydroxycyclopentenones, which are prepared from the furancarbinols [VIII] as is explained hereinafter, with a lower aliphatic carboxylic acid of the formula:

$$R_1'COOH \qquad [X']$$

wherein $R_1'$ is a $C_1$–$C_5$ alkyl having optionally a halogen substituent and an anhydride of said carboxylic acid and further a metal salt of said carboxylic acid.

The aliphatic carboxylic acid [X'] includes, for example, acetic acid, propionic acid, butyric acid, valeric acid, chloroacetic acid, chloropropionic acid, and the like. The metal salt thereof includes lithium salt, sodium salt, potassium salt, calcium salt, copper salt, zinc salt, palladium salt, lead salt, tin salt, manganese salt, cobalt salt, and the like.

The carboxylic acid [X'] is usually used in an amount of one or more equivalents to the starting 3-hydroxycyclopentenones [IX] and/or racemic 4-hydroxycyclopentenones. The amount of the metal salt of the compound [X'] is usually in the range of 0.01 to 5 equivalents, preferably 0.01 to 0.5 equivalent, and that of the acid anhydride of the compound [X'] is usually in one equivalent or more, to the starting 3-hydroxycyclopentenones and/or racemic 4-hydroxycyclopentenones.

In the above reaction, it is important to use simultaneously the three reactants of the carboxylic acid [X'], the anhydride of the carboxylic acid [X'], and the metal salt of the carboxylic acid [X'], and if any one of them is omitted, the reaction proceeds insufficiently. For example, when a mixture of the 3-hydroxycyclopentenones [IX] and the racemic 4-hydroxycyclopentenones or the 3-hydroxycyclopentenones [IX] is reacted without using any anhydride of the carboxylic acid [X'], the reaction product is obtained in the form of a mixture of cyclopentenone esters [XI] and racemic 4-hydroxycyclopentenones and the yield is also lower.

The solvent used in the above reaction includes any conventional aliphatic or aromatic inert solvents, for example, ethers (e.g. tetrahydrofuran, diethyl ether, etc.), ketones (e.g. acetone, methyl ethyl ketone, etc.), aromatic hydrocarbons (e.g. toluene, benzene, etc.), aliphatic hydrocarbons (e.g. hexane, etc.), halogenated aliphatic or aromatic hydrocarbons (e.g. chlorobenzene, dichloromethane, dichloroethane, chloroform, carbon tetrachloride, etc.), aprotic polar solvents (e.g. dimethylformamide, dimethylsulfoxide, etc.), or a mixture of two or more thereof. The amount of the solvent is not critical. The reactant aliphatic carboxylic acid may also be used as a solvent.

The reaction is usually carried out at a temperature of 0° to 150° C., preferably 30° to 140° C., for 0.5 to 10 hours. When the reaction period is longer, the produced cyclopentenone esters [XI] are disadvantageously partially decomposed, and hence, it is desirable to avoid to react for unnecessarily too long period of time.

The reaction can proceed in the following manners:

(1) charging simultaneously all of the starting 3-hydroxycyclopentenones [IX] and/or racemic 4-hydroxycyclopentenones and the aliphatic carboxylic acid [X'], the anhydride of the carboxylic acid [X'], and the metal salt of the carboxylic acid [X'] in a reaction vessel, or (2) charging firstly the starting 3-hydroxycyclopentenones [IX] and/or racemic 4-hydroxycyclopentenones and the aliphatic carboxylic acid [X'] and the anhydride of the [X'] in a reaction vessel, reacting them for an appropriate period of time (usually for 0.1 to 5 hours, but not limited thereto), and thereafter adding thereto the metal salt of the carboxylic acid [X'] and reacting them.

By the above reaction, the desired cyclopentenone esters [XI] can be obtained from the 3-hydroxycyclopentenones [IX] and/or racemic 4-hydroxycyclopentenones easily and in high yield. This product may be purified by a conventional method such as column chromatography, but unpurified product may be used for the subsequent reaction as mentioned hereinabove.

The racemic 4-hydroxycyclopentenones used for the conversion into the cyclopentenone esters [XI] as mentioned hereinbefore can be prepared by subjecting the 3-hydroxycyclopentenones [IX] and/or racemic 4-hydroxycyclopentenones to isomerization reaction which is carried out in an aqueous solvent (mainly water) at pH 6-9 or alternatively in the presence of chloral and an organic amine.

The first racemization reaction is explained below.

The solvent used in the reaction comprises mainly water, that is, water alone, or a mixture of water and an organic solvent. The organic solvent includes any inert aliphatic or aromatic solvents, such as ethers (e.g. dioxane, tetrahydrofuran, diethyl ether, etc.), diols (e.g. ethylene glycol, 1,3-propanediol, etc.), lower alcohols (e.g. methanol, ethanol, etc.), esters (e.g. ethyl acetate, etc.), organic acids (acetic acid, etc.), aromatic hydrocarbons (e.g. toluene, etc.), halogenated aliphatic hydrocarbons (e.g. dichloromethane, dichloroethane, etc.), aprotic polar solvents (e.g. dimethylformamide, dimethylsulfoxide, etc.), or a mixture of two or more thereof. The amount of the solvent is not critical.

The reaction can be carried out without any catalyst, but may preferably be carried out in the presence of a catalyst for promoting the reaction. The catalyst includes various metal salts, organic quaternary ammonium salts, surfactants, alcohols, and the like. Suitable examples of the metal salts are phosphate, sulfate, chloride, bromide, oxide, organic aliphatic acid salt, or organic sulfonic acid salt of metals such as sodium, potassium, magnesium, zinc, iron, calcium, manganese, cobalt, aluminum, and the like. Suitable examples of the organic quaternary ammonium salts are tetrabutylammonium bromide, benzyltrimethylammonium chloride, tricaprylmethylammonium chloride, dodecyltrimethylammonium chloride, caprylbenzyldimethylammonium chloride, and the like. Suitable examples of the surfactants are higher aliphatic salts, polyoxyethylene alkylphenol ethers, higher aliphatic alcohols, and the like. Suitable examples of the alcohols are methanol, ethanol, ethylene glycol, etc. which are used as a solvent as mentioned above. These catalysts may be used alone or in mixture of two or more thereof.

The amount of the catalyst is not critical but is usually in the range of 1/200 to 5 times by weight to the amount of the starting 3-hydroxycyclopentenones [IX] and/or racemic 4-hydroxycyclopentenones. The catalyst may be recovered from the reaction mixture and re-used.

The above reaction is preferably carried out at pH 6-9, more preferably pH 7-9. For adjusting the pH range, there may be used a conventional acid, such as inorganic or organic acids (e.g. hydrochloric acid, sulfuric acid, phosphoric acid, boric acid, acetic acid, propionic acid, toluenesulfonic acid, methanesulfonic acid, etc.), or a conventional alkali, such as inorganic or organic basic substances (e.g. sodium hydroxide, potassium carbonate, sodium hydrogen carbonate, potassium monohydrogen phosphate, organic amines, etc.), or a buffer solution of a combination of the above acid—basic substance, such as combinations of potassium monohydrogen phosphate—phosphoric acid; sodium acetate—acetic acid; sodium acetate—phosphoric acid, phthalic acid—potassium carbonate, potassium monohydrogen phosphate—hydrochloric acid, potassium dihydrogen phosphate—potassium hydrogen carbonate, succinic acid—sodium hydrogen carbonate, and the like. It is usually preferable to avoid use of a strong acid (e.g. hydrochloric acid, hydrobromic acid, etc.) and strong alkali (e.g. sodium hydroxide, potassium hydroxide, etc.).

The reaction is usually carried out at a temperature of 0° to 200° C., preferably 20° to 160° C.

The racemic 4-hydroxycyclopentenones thus produced can be isolated from the reaction mixture by conventional methods such as extraction, liquid separation, concentration, distillation, chromatography, and the like.

The alternative isomerization reaction of the 3-hydroxycyclopentenones [IX] and/or racemic 4-hydroxycyclopentenones can be carried out in the presence of chloral and an organic amine.

The chloral is usually used in an amount of 0.005 to 1 mole, preferably 0.01 to 0.3 mole, to 1 mole of the starting 3-hydroxycyclopentenones [IX].

The organic amine is preferably organic tertiary amines, such as triethylamine, N-methylmorpholine, N-methylpiperidine, N,N'-dimethylpiperazine, pyridine, lutidine, and the like, which may be used alone or in combination of two or more thereof. The amount of the organic amine is not critical but is usually in the range of 0.005 to 0.4 mole to 1 mole of the starting 3-hydroxycyclopentenones [IX] and/or racemic 4-hydroxycyclopentenones.

The reaction may be carried out without using any solvent but may be carried out in an appropriate solvent. The solvent includes any conventional inert aliphatic or aromatic solvents, such as ethers (e.g. tetrahydrofuran, dioxane, diethyl ether, etc.), ketones (e.g. acetone, etc.), esters (e.g. ethyl acetate, etc.), aromatic hydrocarbons (e.g. toluene, benzene, etc.), aliphatic hydrocarbons (e.g. heptane, cyclohexane, etc.), halogenated aliphatic or aromatic hydrocarbons (e.g. chlorobenzene, dichloromethane, dichloroethane, etc.), or a mixture of two or more thereof.

The reaction is usually carried out at a temperature of $-10°$ to 100° C., preferably 0° to 90° C. The reaction period is not critical.

The racemic 4-hydroxycyclopentenones thus produced can be isolated from the reaction mixture by a conventional method such as extraction, liquid separation, concentration. The product may be purified by a conventional method such as column chromatography, but may be used in the unpurified form for the subsequent step.

The racemic 4-hydroxycyclopentenones can alternatively be prepared by treating the cyclopentenone esters [XI] with an alcohol of the formula:

$$R\text{—}OH \qquad\qquad [XII]$$

wherein R is as defined above, in the presence of an acid catalyst.

The alcohol [XII] includes straight chain or branched chain aliphatic alcohols, such as methanol, ethanol, n-propanol, isopropanol, n-butanol, isobutanol, t-butanol, n-pentanol, isopentanol, hexanol, and the like. The alcohol is usually used in an amount of 0.5 to 10 parts by weight to 1 part by weight of the cyclopentenone esters [XI], but may be used over 10 parts by weight. When the amount of the alcohol is less than 0.5 part by weight to 1 part by weight of the cyclopentanone ester, both ester groups of the cyclopentanone ester [XI] are hydrolyzed to give 4-hydroxy-2-(6-carboxy)-2-cyclopentenones as a by-product, and thereby, the desired product is obtained in a lower yield.

The acid catalyst used in the above reaction includes inorganic or organic acids, for example, hydrochloric acid, nitric acid, phosphoric acid, polyphosphoric acid, sulfuric acid, hydrobromic acid, toluenesulfonic acid, methanesulfonic acid, and the like.

These acid catalysts may be used in various forms, such as an aqueous solution or an anhydrous state (e.g. conc. sulfuric acid, hydrogen chloride gas, toluenesulfonic acid, etc.), but are usually used in the form of an aqueous solution. The aqueous solution is usually in a concentration of 10 wt. % or more, preferably 15 wt. % or more of the acid. The upper limit of the acid concentration is controlled depending on the kinds of the acids, i.e. the upper limit is the saturation point of the acid. For instance, the limit is 35 to 37 wt. % in case of hydrochloric acid, 46 to 47 wt. % in case of hydrobromic acid, 60 to 70 wt. % in case of phosphoric acid and nitric acid, up to 98 wt. % in case of sulfuric acid. However, in case of sulfuric acid, it is preferable to use in a concentration of up to 80 wt. % in view of prevention of by-product and lower yield.

When an acid catalyst having a concentration of less than 10 wt. % is used, the acid catalyst is required in too much amount to the starting cyclopentenone esters [XI], and hence, it is required to raise the reaction temperature in order to promote the reaction, which induces disadvantageously lowering of yield and increase of by-product. Besides, when sulfuric acid having a concentration of more than 80% is used, it is preferable to use the catalyst in an amount as small as possible and further to keep the reaction temperature as lower as possible in order to increase the yield of the product and to decrease the by-product.

The acid catalyst is usually used in an amount of 0.05 to 3 parts by weight to 1 part by weight of the starting cyclopentenone ester (XI), and the most suitable amount is determined within said range in accordance with the concentration of the acid catalyst.

The reaction is usually carried out at a temperature of $-10°$ to $80°$ C., preferably $0°$ to $60°$ C., for 12 hours or shorter.

The reaction can also be carried out by using a solvent. The solvent includes any conventional inert aliphatic or aromatic solvent, for example, ethers (e.g. tetrahydrofuran, dioxane, diethyl ether, etc.), ketones (e.g. acetone, etc.), aromatic hydrocarbons (e.g. toluene, benzene, etc.), aliphatic hydrocarbons (e.g. hexane, etc.), halogenated aliphatic hydrocarbons (e.g. dichloromethane, chloroform, etc.), aprotic polar solvents (e.g. dimethylsulfoxide, dimethylformamide, etc.), or a mixture of two or more thereof, but preferably a water-soluble solvent miscible with the acid catalyst, such as tetrahydrofuran, dioxane, acetone, dimethylformamide, and the like. The alcohol [XII] may also be used as the solvent. When only the alcohol [XII] is used as the solvent, the separation of the solvent can easily be done after the completion of the reaction. Thus, in the preferred feature, the reaction is carried out by using only the starting cyclopentenone ester [XI], the alcohol [XII] and an acid catalyst.

After completion of the reaction, the desired racemic 4-hydroxycyclopentenones can be isolated in high yield and high purity by the steps of pouring the reaction mixture into ice water, and subjecting to the usual after-treatment such as extaction or neutralization, distilling off of the solvent, extraction, concentration, and the like. The product may optionally be purified by a conventional method such as distillation, column chromatography, and the like.

The 3-hydroxycyclopentenones [IX] and/or racemic 4-hydroxycyclopentenones used for the preparation of the cyclopentanone esters [XI] as described above can be prepared from furancarbinols [VIII] by subjecting the compounds to rearrangement in an aqueous solvent at pH 3.5-6 in the presence or absence of a catalyst.

When the reaction is carried out at a comparatively lower pH range such as pH 3.5-4.3 within a comparatively shorter period of time, the reaction product comprises mainly 3-hydroxycyclopentenones [IX]. With prolonging the reaction period of time, the isomerization from the 3-hydroxycyclopentenones [IX] to the racemic 4-hydroxycyclopentenones progresses, and finally the product becomes racemic 4-hydroxycyclopentenones. However, the racemic 4-hydroxycyclopentenones are more easily prepared by the isomerization methods as described hereinbefore.

The solvent used in the above rearrangement reaction comprises mainly water, that is, water alone, or a mixture of water and an organic solvent. The organic solvent includes any inert aliphatic or aromatic solvents, such as ethers (e.g. dioxane, tetrahydrofuran, diethyl ether, etc.), diols (e.g. ethylene glycol, 1,3-propanediol, etc.), lower alcohols (e.g. methanol, ethanol, etc.), esters (e.g. ethyl acetate, etc.), organic acids (acetic acid, etc.), aromatic hydrocarbons (e.g. toluene, etc.), halogenated aliphatic hydrocarbons (e.g. dichloromethane, dichloroethane, etc.), aprotic polar solvents (e.g. dimethylformamide, dimethylsulfoxide, etc.), or a mixture of two or more thereof.

The reaction can be carried out without any catalyst, but may preferably be carried out in the presence of a catalyst for promoting the reaction. The catalyst includes various metal salts, organic quaternary ammonium salts, surfactants, alcohols, and the like. Suitable examples of the metal salts are phosphate, sulfate, chloride, bromide, oxide, organic aliphatic acid salt, or organic sulfonic acid salt of metals such as sodium, potassium, magnesium, zinc, iron, calcium, manganese, cobalt, aluminum, and the like. Suitable examples of the organic quaternary ammonium salts are tetrabutylammonium bromide, benzyltrimethylammonium chloride, tricaprylmethylammonium chloride, dodecyltrimethylammonium chloride, caprylbenzyldimethylammonium chloride, and the like. Suitable examples of the surfactants are higher aliphatic salts, polyoxyethylene alkylphenol ethers, higher aliphatic alcohols, and the like. Suitable examples of the alcohols are methanol, ethanol, ethylene glycol, etc. which are used as a solvent as mentioned above. These catalysts may be used alone or in mixture of two or more thereof.

The amount of the catalyst is not critical but is usually in the range of 1/200 to 5 times by weight to the amount of the furancarbinols [VIII]. The catalyst may be recovered from the reaction mixture and re-used.

The above reaction is preferably carried out at pH 3.5-6, more preferably pH 3.5-5.5. For adjusting the pH range, there may be used a conventional acid, such as inorganic or organic acids (e.g. hydrochloric acid, sulfuric acid, phosphoric acid, boric acid, acetic acid, propionic acid, toluenesulfonic acid, methanesulfonic acid, etc.), or a conventional alkali, such as inorganic or organic basic substances (e.g. sodium hydroxide, potassium carbonate, sodium hydrogen carbonate, potassium monohydrogen phosphate, organic amines, etc.), or a buffer solution of a combination of the above acid—basic substance, such as combinations of potassium monohydrogen phosphate—phosphoric acid; sodium acetate—acetic acid; sodium acetate—phosphoric acid, phthalic acid—potassium carbonate, potassium monohydrogen phosphate—hydrochloric acid, potassium dihydrogen phosphate—potassium hydrogen carbonate, succinic acid—sodium hydrogen carbonate, and the like. It is usually preferable to avoid use of a strong acid (e.g. hydrochloric acid, hydrobromic acid, etc.) and strong alkali (e.g. sodium hydroxide, potassium hydroxide, etc.).

The reaction is usually carried out at a temperature of 0° to 200° C., preferably 20° to 160° C.

The 3-hydroxycyclopentenones and/or racemic 4-hydroxycyclopentenones thus produced can be isolated from the reaction mixture by conventional methods such as extraction, liquid separation, concentration, distillation, and the like. The products thus obtained can be used for the subsequent process as they stand.

The furancarbinols [VIII] used in the above reaction can be prepared by treating the furfuryl ketones VII] with a reducing agent.

The reducing agent includes an agent which is inert to an ester group and unsaturated bond and can reduce only ketone, for example, metal hydrides such as sodium borohydride, lithium borohydride, potassium borohydride, zinc borohydride, sodium cyanoborohydride, sodium trimethoxyborohydride, t-butoxylithium aluminum hydride, and the like.

The reaction is preferably carried out in an appropriate inert solvent, such as alcohols (e.g. methanol, ethanol, isopropyl alcohol, etc.), ethers (e.g. tetrahydrofuran, dioxane, diethyl ether, 1,2-dimethoxyethane, etc.), halogenated hydrocarbons (e.g. dichloromethane, chloroform, etc.).

The reaction is usually carried out at a temperature of $-20°$ to 50° C., preferably $-15°$ to 30° C. The reaction period of time is not critical, but when the starting furfuryl ketones [VII] are consumed and disappear, the reaction is completed.

The reaction is advantageously carried out in the presence of a basic substance because the reduction proceeds more effectively. The basic substance includes inorganic and organic basic substances. Suitable examples are inorganic compounds such as alkali metal methylates (e.g. sodium methylate, potassium methylate, etc.), alkali metal hydroxides (e.g. sodium hydroxide, potassium hydroxide, etc.), and organic compounds such as organic amines (e.g. trimethylamine, triethylamine, pyridine, N,N-dimethylaniline, N,N-diethylaniline, etc.). These basic substances are usually used in an amount of 0.01 to 20 % by weight, preferably 0.05 to 5 % by weight, based on the amount of the fufuryl ketone [VII].

After the completion of the reaction, the furancarbinols [VIII] can be isolated from the reaction mixture by the steps of removing the excess reducing agent, and subjecting to conventional treatment such as extraction, liquid separation, concentration, and the like. The product may be purified by a conventional method such as column chromatography, but the crude product may be used for the subsequent step as it stands.

The fufuryl ketones [VII] can be prepared by condensing the half esters [VI] with furan in the presence of trifluoroacetic anhydride, or by condensing the half esters [VI] with an acid anhydride of the formula:

$$(XYCHCO)_2O \qquad [XIII]$$

wherein X and Y are the same or different and are each hydrogen atom, chlorine atom, or bromine atom, provided that both X and Y are not simultaneously hydrogen atom, in the presence of a catalyst of boron trifluoride or boron trifluoride complex.

The reaction is usually carried out in a solvent. The solvent includes conventional inert solvents, for example, toluene, xylene, dichloromethane, dichloroethane, chloroform, carbon tetrachloride, and the like, which are used alone or in combination of two or more thereof. The solvent is usually used in an amount of 1 to 20 parts by weight to 1 part by weight of the half esters [VI].

The trifluoroacetic anhydride or the acid anhydride [XIII] is used in an amount of one equivalent or more, preferably 1.1 to 1.3 equivalent, to the half esters [VI].

The acid anhydride [XIII] includes chloroacetic anhydride, bromoacetic anhydride, dichloroacetic anhydride, and the like.

The catalyst includes boron trifluoride and boron trifluoride complexes, but preferably boron trifluoride complexes such as $BF_3$—$(C_2H_5)_2O$, $BF_3$—$2CH_3OH$, $BF_3$—$CH_3COOH$, and the like.

The furan is usually used in an amount of one equivalent or more, preferably 1.2 to 4 equivalents, to the half esters [VI]. The catalyst, boron trifluoride or boron trifluoride complex is usually used in an amount of 0.02 to 0.2 equivalent to the half ester [VI], but it is not limited thereto and a larger amount of the catalyst may be used.

The reaction is usually carried out at a temperature of $-5°$ to 150° C., preferably 10° to 75° C. The reaction period of time may vary depending on the reaction conditions but is usually in the range of 0.5 to 20 hours.

The furfuryl ketones [VII] thus prepared can be isolated from the reaction mixture by a conventional treatment such as extraction, liquid separation, concentration, and the like, and may optionally be purified by a conventional method such as column chromatography, but unpurified product may be used for the subsequent step.

The half esters [VI] used in the above reaction can be prepared by reacting the diesters [II] with an alkaline earth metal, followed by separating by addition of an acid thereto.

The diesters [II] include, for example, 1,6-dicarbomethoxy-3-hexyne, 1,6-dicarbomethoxy-3-hexene, 1,6-dicarboethoxy-3-hexyne, 1,6-dicarboethoxy-3-hexene, 1,6-dicarbopropoxy-3-hexyne, 1,6-dicarbopropoxy-3-hexene, 1,6-dicarbobutoxy-3-hexyne, 1,6-dicarbobutoxy-3-hexene, 1,6-dicarbopentyloxy-3-hexyne, 1,6-dicarbopentyloxy-3-hexene, 1,6-dicarbohexyloxy-3-hexyne, 1,6-dicarbohexyloxy-3-hexene, and the like.

The alkaline earth metal used therein includes calcium hydroxide, barium hydroxide, preferably barium hydroxide in view of the solubility. The alkaline earth metal is usually used in an amount of 0.1 to 1.5 mole, preferably 0.7 to 1.3 mole, to 1 mole of the diesters [II].

The reaction can be carried out in an appropriate solvent, which can preferably dissolve the alkaline earth metal, for example, alcohols (e.g. methanol, ethanol, etc.), non-aqueous polar solvents (e.g. dimethylacetamide, dimethylformamide, N-methylpyrrolidone, dimethylsulfoxide, etc.), water, and a mixture of these solvents.

The reaction is usually carried out at a temperature of −20° to 200° C., preferably −10° to 50° C.

The produced salt of the half esters [VI] can be isolated from the reaction mixture by a conventional method such as filtration.

The acid is any acids which can decompose the formed salt of half esters [VI] and includes, for example, hydrochloric acid, sulfuric acid, nitric acid, phosphoric acid, and the like, preferably hydrochloric acid which can form an easily soluble salt with the alkaline earth metal.

The separation of the produced half esters [VI] can easily be done by using a solvent. The solvent includes aromatic hydrocarbons (e.g. benzene, toluene, xylene, etc.), aliphatic hydrocarbons (e.g. n-hexane, n-heptane, etc.), ethers (e.g. diethyl ether, diisopropyl ether, etc.), esters (e.g. methyl acetate, ethyl acetate, etc.), halogenated aliphatic or aromatic hydrocarbons (e.g. chloroform, 1,2-dichloroethane, chlorobenzene, etc.), or a mixture of two or more thereof.

After decomposing of the salt with an acid, the produced half esters [VI] are separated from the reaction mixture by a conventional treatment such as extraction, concentration, and the like. The product may be purified by a conventional method such as recrystallization but may be used in the form of a crude product for the subsequent step.

When the diesters having a triple bond (the symbol $\chi$ in the formula [II] is triple bond), that is, the compounds of the formula [II-1]:

[II-1]

wherein R is as defined above, is used for producing the desired optically active 4-hydroxycyclopentenones of the formula [I] wherein the symbol ≐ is double bond, any compound of the formulae [II-1], [VI], [VII], [VIII], [IX] and/or racemic 4-hydroxycyclopentenones, racemic 4-hydroxycyclopentenones, or a compound of the formula [XI] (wherein the symbol ≐ is triple bond) is subjected to partial hydrogenation to give the corresponding compound having double bond as the symbol ≐, and further the thus-obtained compound having double bond as the symbol ≐ is subjected to the subsequent reactions as mentioned above to give the desired optically active 4-hydroxycyclopentenones [I] wherein the group ≐ is double bond. The partial hydrogenation may also be done at the final step, that is, the optically active 4-hydroxycyclopentenones [I] wherein the symbol ≐ is triple bond is prepared and then subjected to the partial hydrogenation to give the desired optically active 4-hydroxycyclopentenones [I] wherein the symbol ≐ is double bond.

As to the case of using optically active 4-hydroxycyclopentenones of the formula [I-1]:

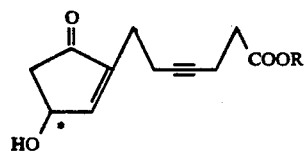

[I-1]

wherein R and the * marked carbon are as defined above, the partial hydrogenation is illustrated below, but as to the other compounds it is also carried out in the same manner.

The partial hydrogenation is usually carried out by treating the optically active 4-hydroxycyclopentenones [I-1] with a hydrogenating catalyst in an appropriate solvent.

The hydrogenating catalyst includes catalysts which has less activity so as to be inactive to double bond and hence can selectively reduce triple bond to give cis double bond. Suitable examples of the catalyst are so-called Lindlar catalyst, such as palladium-lead, palladium-barium sulfate, palladium-lead-calcium carbonate, palladium-calcium carbonate-lead oxide, and the like. The catalyst is usually used in an amount of 0.001 to 0.5 part by weight, preferably 0.005 to 0.3 part by weight, to 1 part by weight of the optically active 4-hydroxycyclopentenones [I-1].

The solvent used therein includes any inert solvents, for example, water, ethers (e.g. dioxane, tetrahydrofuran, diethyl ether, etc.), alcohols (e.g. methanol, ethanol, n-propyl alcohol, etc.), ketones (e.g. acetone, etc.), aromatic hydrocarbons (e.g. toluene, etc.), aliphatic hydrocarbons (e.g. hexane, etc.), halogenated aliphatic hydrocarbons (e.g. dichloromethane, etc.), esters (e.g. ethyl acetate, etc.), aprotic polar solvents (e.g. dimethylformamide, etc.), or a mixture of two or more thereof.

The reaction is usually carried out at a temperature of −10° to 100° C., preferably 10° to 60° C., under atmospheric pressure or under pressure. When the starting optically active 4-hydroxycyclopentenones [I-1] are consumed and disappear from the reaction system, or when the absorption of hydrogen gas becomes 1 to 1.1 equivalent to the starting optically active 4-hydroxycyclopentenones [I-1], the reaction is deemed to be completed. Too excess reduction is not favorable in view of the selectivity of the reduction.

After completion of the reaction, the catalyst is removed by filtration, and the reaction mixture is subjected to a conventional treatment such as concentration, to give the desired optically active 4-hydroxycyclopentenones having double bond of the formula [I-2]:

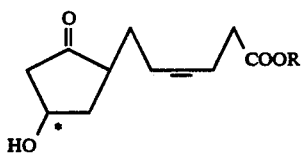

[I-2]

wherein R and the * marked carbon are as defined above. The product may optionally be purified by a conventional method such as column chromatography.

The diesters [II-1] can be prepared by reacting the acetylene derivative [III]:

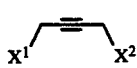

[III]

wherein $X^1$ and $X^2$ are each chlorine atom, bromine atom, iodine atom, methanesulfonyloxy, or p-toluenesulfonyloxy, with the acetoacetic acid ester [IV]:

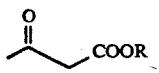 [IV]

wherein R is as defined above, in the presence of a metal alkoxide.

The acetylene derivative [III] includes, for example, 1,4-dichloro-2-butyne, 1,4-dibromo-2-butyne, 1,4-diiodo-2-butyne, 1,4-dimethanesulfonyloxy-2-butyne, 1,4-di-(p-toluenesulfonyloxy)-2-butyne, 1-bromo-4-chloro-2-butyne, 1-chloro-4-iodo-2-butyne, 1-bromo-4-iodo-2-butyne, and the like.

The acetoacetic acid ester [IV] includes, for example, methyl acetoacetate, ethyl acetoacetate, n-propyl acetoacetate, isopropyl acetoacetate, n-butyl acetoacetate, n-pentyl acetoacetate, n-hexyl acetoacetate, and the like. Acetoacetate having 7 or more carbon atoms in the ester moiety may also be used.

The metal alkoxide used in the above reaction includes, for example, sodium methoxide, sodium ethoxide, potassium methoxide, potassium t-butoxide, and the like.

These acetylene derivative [III], acetoacetic ester [IV] and metal alkoxide may be charged into the reaction vessel in any manner, that is, they may be charged into the reaction vessel at one time, in portions, simultaneously or separately, and additional amount of the metal alkoxide may optionally be added during the reaction.

The reaction may also be carried out in a solvent unless it affects on the reaction. The solvent includes, for example, aromatic hydrocarbons (e.g. benzene, toluene, xylene, etc.), aliphatic hydrocarbons (e.g. pentane, hexane, etc.), esters (e.g. methyl acetate, ethyl acetate, etc.), alcohols (e.g. methanol, ethanol, etc.), ethers (e.g. diethyl ether, diisopropyl ether, etc.), and the like. These may be used in a combination of two or more at an appropriate ratio.

The acetoacetic acid ester [IV] is usually used in an amount of 1 to 10 moles, preferably 2 to 4 moles, to 1 mole of the acetylene derivative [III]. The metal alkoxide is usually used in an amount of 0.5 to 10 moles, preferably to 4 moles, to 1 mole of the acetoacetic acid ester [IV].

The reaction is usually carried out at a temperature of 20° C. or higher, preferably 50° to 150° C. The reaction period is not critical.

After the completion of the reaction, the produced diesters [II-1] can be isolated from the reaction mixture by conventional treatment, such as removal of solvent by distillation, washing, extraction, concentration, and the like. The product may be purified by a conventional method such as distillation under reduced pressure.

The diesters [II-1] can alternatively be prepared by treating the acetoacetic acid derivative [V], which is prepared from the acetylene derivative [III] and acetoacetic acid [IV] as described hereinafter, with a metal alkoxide.

The acetoacetic acid derivative [V] includes, for example, 3,8-dimethoxycarbonyl-5-decyne-2,9-dione, 3,8-diethoxycarbonyl-5-decyne-2,9-dione, 3,8-dipropoxycarbonyl-5-decyne-2,9-dione, 3,8-dibutoxycarbonyl-5-decyne-2,9-dione, 3,8-dipentyloxycarbonyl-5-decyne-2,9-dione, 3,8-dihexyloxycarbonyl-5-decyne-2,9-dione, and the like.

The metal alkoxide used in the above reaction includes, for example, sodium methoxide, sodium ethoxide, potassium methoxide, potassium t-butoxide, and the like.

These acetoacetic acid derivative [V] and metal alkoxide may be charged into the reaction vessel in any manner, that is, they may be charged into the reaction vessel at one time, in portions, simultaneously or separately, and additional amount of the metal alkoxide may optionally be added during the reaction. The metal alkoxide is usually used in an amount of 0.01 to 10 moles, preferably 0.1 to 1 mole, to 1 mole of the acetoacetic acid derivative [V].

The reaction may also be carried out in a solvent unless it affects on the reaction. The solvent includes, for example, aromatic hydrocarbons (e.g. benzene, toluene, xylene, etc.), aliphatic hydrocarbons (e.g. pentane, hexane, etc.), esters (e.g. methyl acetate, ethyl acetate, etc.), alcohols (e.g. methanol, ethanol, etc.), ethers (e.g. diethyl ether, diisopropyl ether, etc.), and the like. These may be used in a combination of two or more at an appropriate ratio.

The reaction is usually carried out at a temperature of 0° C. or higher, preferably 20° to 100° C. The reaction period is not critical, and when the staring acetoacetic acid derivative [V] is consumed and disappears from the reaction system, the reaction is deemed to be completed.

After the completion of the reaction, the produced diesters [II-1] can be isolated from the reaction mixture by conventional treatment, such as removal of solvent by distillation, washing, extraction, concentration, and the like. The product may be purified by a conventional method such as distillation under reduced pressure.

The acetoacetic acid derivative [V] used in the above reaction can be prepared by reacting the acetylene derivative [III] and the acetoacetic acid ester [IV] in the presence of a metal carbonate.

The same acetylene derivatives [III] and acetoacetic acid esters [VI] as listed hereinbefore can be used in this reaction.

The metal carbonate used in this reaction includes, for example, potassium carbonate, sodium carbonate, and the like.

These acetylene derivative [III], acetoacetic ester [IV] and metal carbonate may be charged into the reaction vessel in any manner, that is, they may be charged into the reaction vessel at one time, in portions, simultaneously or separately, and additional amount of the metal carbonate may optionally be added during the reaction.

The reaction may also be carried out in a solvent unless it affects on the reaction. The solvent includes, for example, aromatic hydrocarbons (e.g. benzene, toluene, xylene, etc.), aliphatic hydrocarbons (e.g. pentane, hexane, etc.), esters (e.g. methyl acetate, ethyl acetate, etc.), alcohols (e.g. methanol, ethanol, etc.), ethers (e.g. diethyl ether, diisopropyl ether, etc.), and the like. These may be used in a combination of two or more at an appropriate ratio.

The acetoacetic acid ester [IV] is usually used in an amount of 1 to 10 moles, preferably 2 to 4 moles, to 1 mole of the acetylene derivative [III]. The metal carbonate is usually used in an amount of 0.5 to 10 moles, preferably 1 to 4 moles, to 1 mole of the acetoacetic acid ester [IV].

The reaction is usually carried out at a temperature of 20° C. or higher, preferably 50° to 150° C. The reaction period is not critical, and when the starting acetylene derivative [III] is consumed and disappears from the reaction system, the reaction is deemed to be completed.

After the completion of the reaction, the produced acetoacetic acid derivative [V] can be isolated from the reaction mixture by conventional treatment, such as removal of solvent by distillation, washing, extraction, concentration, and the like. The product may be purified by a conventional method such as distillation under reduced pressure.

EFFECTS OF THE INVENTION

The process of this invention can provide the desired optically active 4-hydroxycyclopentenones [I] and also racemic 4-hydroxycyclopentenones via novel intermediates in a high yield on an industrial scale and further with a high optical purity, and further can provide the diesters [II-1] which are useful as an intermediate for preparing the desired optically active 4-hydroxycyclopentenones [I] and racemic 4-hydroxycyclopentenones easily and on industrial scale.

This invention illustrated by the following Examples but should not be construed to be limited thereto.

EXAMPLE 1

Toluene (796 g) is added to 1,4-dichloro-2-butyne (200 g, 1.63 mole), and to the mixture is added a mixture of methyl acetoacetate (568 g, 4.89 mole) and 28 % solution of sodium methylate in methanol (896 g, 4.65 mole) at room temperature. The reaction temperature is raised to 60° C., and the mixture is stirred for 16 hours. After completion of the reaction, the mixture is concentrated under reduced pressure, and methanol is removed therefrom. Water (1.5 liter) and toluene (1 liter) are added to the resulting residue, and the mixture is stirred. The aqueous layer is removed, and the toluene layer is washed with water (1.5 liter). The toluene layer is concentrated under reduced pressure, and further evaporated under reduced pressure to give 1,6-dicarbomethoxy-3-hexyne (109.7 g, content; 95.8%).

EXAMPLE 2

To methyl acetoacetate (757 g, 6.52 mole) is added 28 % solution of sodium methylate in methanol (1258 g, 6.52 mole), and the mixture is cooled to room temperature. To the mixture is added 1,4-dichloro-2-butyne (200 g, 1.63 mole). The reaction temperature is raised to 60° C., and the mixture is stirred for 16 hours. After completion of the reaction, the reaction mixture is concentrated under reduced pressure, and methanol is removed therefrom. Water (2 liters) and toluene (1 liter) are added to the resulting residue, and the mixture is stirred. The aqueous layer is removed, and the toluene layer is washed with water (2 liters). The toluene layer is concentrated under reduced pressure, and further evaporated under reduced pressure to give 1,6-dicarbomethoxy-3-hexyne (96.4 g, content; 93.7 %).

EXAMPLE 3

Toluene (796 g) is added to 1,4-dichloro-2-butyne (200 g, 1.63 mole), and to the mixture is added a mixture of methyl acetoacetate (568 g, 4.89 mole) and 28 % solution of sodium methylate in methanol (942 g, 4.89 mole) at room temperature. The reaction temperature is raised to 64° C., and the mixture is stirred for 9 hours. To the mixture is added additional 28 % solution of sodium methylate in methanol (94.2 g. 0.489 mole). The mixture is further stirred at 64° C. for 6 hours. After completion of the reaction, the mixture is concentrated under reduced pressure, and methanol is removed therefrom. Water (1.5 liter) and toluene (1 liter) are added to the resulting residue, and the mixture is stirred. The aqueous layer is removed, and the toluene layer is washed with water (1.5 liter). The toluene layer is concentrated under reduced pressure, and further evaporated under reduced pressure to give 1,6-dicarbomethoxy-3-hexyne (117.3 g, content; 96.3%).

EXAMPLE 4

Methyl acetoacetate (144.5 g, 1.245 mole), 1,4-dichloro-2-butyne (67.7 g, 0.550 mole) and toluene (500 g) are charged in a flask, and the mixture is warmed to 80° C. To the mixture is added potassium carbonate (100 g) and the mixture is stirred at 80° C. for 1.5 hour. Further, to the mixture is added additional potassium carbonate (104 g) and the mixture is stirred at 80° C. for 8 hours. To the mixture are added methyl acetoacetate (21.5 g, 0.185 mole) and potassium carbonate (51.1 g), and the mixture is reacted with stirring for 4 hours. After completion of the reaction, the resulting precipitates are removed by filtration, and the filtrate is neutralized with 10 % hydrochloric acid, washed with water, and concentrated under reduced pressure. The resulting residue is evaporated under reduced pressure to give 3,8-dimethoxycarbonyl-5-decyne-2,9-dione (44.4 g, content; 84.3 %), b.p. 168°–172° C.

EXAMPLE 5

3,8-Dimethoxycarbonyl-5-decyne-2,9-dione (11.7 g, content; 84.3 %) obtained in Example 4 and toluene (60 g) are charged in a flask, and thereto is added 28 % solution of sodium methylate in methanol (60 g). The mixture is heated to 70°–73° C., and reacted for 13 hours. After completion of the reaction, the reaction solution is concentrated under reduced pressure. To the residue are added toluene (100 g) and water (100 g) and the mixture is shaken in order to separate the toluene layer. The toluene layer is washed with water (100 g) and concentrated under reduced pressure. The residue is evaporated under reduced pressure to give 1,6-dicarbomethoxy-3-hexyne (2.89 g, content; 94.5%).

EXAMPLE 6

1,6-Dicarbomethoxy-3-hexyne (20.0 g, content; 83.9 0.0847 mole) is dissolved in methanol (40 g) and the mixture is cooled to 5° C. To the mixture is added 2 N anhydrous barium hydroxide (33.9 g) and the mixture is stirred. After stirring for 17 hours, the reaction mixture is filtered, and dried under reduced pressure. The resulting crystal is suspended in 1,2-dichloroethane (100 g) and thereto are added 10 % hydrochloric acid (16 g) and water (50 g). The reaction temperature is raised to 40°–45° C., and the mixture is stirred for 2 hours and then separated. The organic layer is washed with water (50 g) and concentrated under reduced pressure to give 6-methoxycarbonyl-1-carboxy-3-hexyne [VI-1] (12.5 g, yield; 80.2%), m.p. 71.5°–72.0° C.

EXAMPLE 7

To a mixture of 6-methoxycarbonyl-1-carboxy-3-hexyne [VI-1] (27.6 g, 0.15 mole) obtained in Example 6, furan (30.7 g, 0.45 mole) and dichloromethane (150 ml) is added trifluoroacetic anhydride (37.8 g, 0.18 mole) at room temperature. The mixture is reacted at 30°–35° C. for 24 hours.

After completion of the reaction, the reaction mixture is poured into ice-water, and the mixture is neutralized with 20 % aqueous sodium hydroxide solution. The organic layer is separated, and washed successively with 5 % aqueous sodium hydrogen carbonate solution and water. The organic layer is concentrated under reduced pressure to give 1-oxo-1-furyl-7-methoxycarbonyl-4-heptyne [VII-1] (32.3 g, yield; 92%).

$n_D^{25}$ 1.5164.

Subsequently, to a mixture of the compound [VII-1] (30.4 g, 0.13 mole) obtained above, methanol (150 ml) and 28% solution of sodium methylate in methanol (1.5 g) is added sodium borohydride (2.46 g, 0.065 mole) at 5° C. The mixture is stirred at the same temperature for 3 hours, and further at 10°-15° C. for 2 hours. After completion of the reaction, the reaction mixture is poured into ice-water, and extracted with toluene. The organic layer is separated and washed with water, and further concentrated to give 1-hydroxy-1-furyl-7-methoxycarbonyl-4-heptyne [VIII-1] (29.2 g, yield; 95%).

$n_D^{25}$ 1.5082.

To the compound [VIII-1] (28.3 g, 0.12 mole) obtained above are added water (1200 g) and acetic acid (1.5 g), and the pH value thereof is adjusted to pH 4.4 with 5 % aqueous sodium hydroxide solution. The mixture is heated, with stirring at 100° C. for 25 hours. After completion of the reaction, the reaction solution is cooled and extracted twice with methyl isobutyl ketone (300 ml). The extract is separated and concentrated to give a mixture (21.5 g, yield; 76 %) of 4-hydroxy-2-(6-methoxycarbonyl-3-hexynyl)-2-cyclopentenone (racemic 4-hydroxycyclopentenone) and 3-hydroxy-2-(6-methoxycarbonyl-3-hexynyl)-2-cyclopentenone [IX-1] (ratio thereof=6:4).

A mixture of the mixture (9.45 g, 0.04 mole) of the racemic 4-hydroxycyclopentenone and the compound [IX-1] obtained above, acetic acid (14 g), acetic anhydride (4 g) and sodium acetate (0.2 g) is reacted at 115°-120° C. for 4 hours. The reaction solution is checked by gas chromatography, and when the starting materials are not detected therein, the reaction is completed. The reaction solution is concentrated under reduced pressure, and to the resulting residue are added toluene (100 ml) and water (50 ml). The organic layer is separated and washed successively with 8% aqueous sodium hydrogen carbonate solution and water, dried over anhydrous magnesium sulfate, and further concentrated to give 4-acetoxy-2-(6-methoxycarbonyl-3-hexynyl)-2-cyclopentenone [XI-1] (10.5 g, yield; 94.5 %), b.p. 170°-175° C./0.5-0.6 mmHg.

4-Acetoxy-2-(6-methoxycarbonyl-3-hexynyl)-2-cyclopentenone [XI-1] (4.17 g) obtained above, dichloromethane (2 ml), Arthrobacter Lipase (manufactured by Shin-Nippon Kagaku K.K.) (60 mg) and 0.2 M phosphate buffer (pH 7.5, 50 ml) are charged in a flask and the mixture is vigorously stirred at 35°-40° C. for 15 hours. After completion of the reaction, the reaction mixture is extracted twice with methyl isobutyl ketone (40 ml), and the extracts are combined and concentrated under reduced pressure to give the residue (4.02 g). The residue is purified by column chromatography (solvent; toluene:ethyl acetate =5:3) to give the following compounds.

4R(+)-hydroxy-2-(6-methoxycarbonyl-3-hexynyl)-2-cyclopentenone (1.24 g)

$[\alpha]_D^{20}$+18.1° (c=1, CHCl₃) (97.8 % e.e.)

4S(−)-acetoxy-2-(6-methoxycarbonyl-3-hexynyl)-2-cyclopentenone (2.59 g)

$[\alpha]_D^{20}$−29.2° (c=1, CHCl₃).

A mixture of 4R(+)-hydroxy-2-(6-methoxycarbonyl-3-hexynyl)-2-cyclopentenone (1.18 g) obtained above, a Lindlar catalyst (5% Pd-CaCO₃-PbO) (60 mg), cyclohexene (0.5 g) and toluene (30 ml) is charged to an atmospheric hydrogenation apparatus, and subjected to reduction at room temperature under atmospheric pressure. The reduction is completed in 1 hour. After completion of the reaction, the catalyst is removed by filtration, and the filtrate is concentrated. The resulting residue is purified by silica gel column chromatography to give 4R(+)-hydroxy-2-(6-methoxycarbonyl-3-cis-hexenyl)-2-cyclopentenone (1.14 g, yield; 96%).

$[\alpha]_D^{20}$+19.4° (c=1, CHCl₃) (97.8% e.e.).

EXAMPLE 8

A mixture of 6-methoxycarbonyl-1-carboxy-3-hexyne [VI-1] (18.4 g, 0.1 mole), furan (13.6 g, 0.2 mole), dichloroacetic anhydride (28.8 g, 0.12 mole), boron trifluoride ether complex (3.2 g) and toluene (100 ml) is reacted at 20°-30° C. for 10 hours. After completion of the reaction, the reaction mixture is cooled and washed successively with water, 5% aqueous sodium carbonate solution and water. The organic layer is dried over anhydrous magnesium sulfate, concentrated under reduced pressure, and purified by silica gel column chromatography to give 1-oxo-1-furyl-7-methoxycarbonyl-4-heptyne [VII-1] (15.2 g), b.p. 120°-125° C./0.3 mmHg.

A mixture of the compound [VII-1] (14.1 g, 0.06 mole) obtained above, sodium trimethoxyborohydride (10 g, 0.078 mole) and dimethoxyethane (100 ml) is stirred at room temperature. After confirming the disappearance of the starting materials, the reaction solution is poured into ice-water, and extracted twice with ethyl acetate (100 ml). The extract is washed with water and concentrated to give 1-hydroxy-1-furyl-7-methoxycarbonyl-4-heptyne [VIII-1] (13.7 g, yield; 96.5%).

The compound [VIII-1] (11.8 g, 0.05 mole) and a buffer (pH 4.2) consisting of water (500 g), dipotassium hydrogen phosphate (0.3 g) and phosphoric acid are charged to a flask, and the mixture is heated with stirring at 100° C. under nitrogen atmosphere until the starting materials are consumed. In the reaction mixture, there is obtained a mixture of 3-hydroxy-2-(6-methoxycarbonyl-3-hexynyl)-4-cyclopentenone [IX-1] and 4-hydroxy-2-(6-methoxycarbony-3-hexynyl)-2-cyclopentenone (racemic 4-hydroxycyclopentenone).

The reaction mixture is cooled, and the pH value thereof is adjusted to pH 7.6 with 1 N aqueous potassium hydroxide solution. The mixture is heated with stirring at 00° C. under nitrogen atmosphere until 3-hydroxy-2-(6-methoxycarbonyl-3-hexynyl)-4-cyclopentenone [IX-1] obtained in the previous reaction is consumed. After completion of the reaction, the reaction mixture is cooled, extracted twice with methyl isobutyl ketone (600 g) and separated. Methyl isobutyl ketone is distilled off from the organic layer to give 4-hydroxy-2-(6-methoxycarbonyl-3-hexynyl)-2-cyclopentenone (racemic 4-hydroxycyclopentenone) (8.1 g, yield; 69%).

A mixture of the above compound (7.09 g, 0.03 mole), acetic anhydride (4.59 g, 0.045 mole), conc. sulfuric acid (0.1 g) and methyl isobutyl ketone (20 ml) is stirred at 40° C. for 3 hours. After completion of the reaction, the reaction solution is cooled, poured into ice-water and extracted with methyl isobutyl ketone (30 ml). The extract is washed successively with 5% aqueous sodium hydrogen carbonate solution and water, and concentrated to give 4-acetoxy-2-(6-methoxycarbonyl-3-hexynyl)-2-cyclopentenone [XI-1] (8.35 g, yield; 96%).

The compound [XI-1] (4.17 g), Arthrobacter Lipase (manufactured by Shin-Nippon Kagaku K.K.) (80 mg) and 0.2 M phosphate buffer (pH 7.0, 80 ml) are charged in a flask, and the mixture is stirred at 25°–30° C. for 20 hours. After completion of the reaction, the reaction mixture is extracted twice with methyl isobutyl ketone (40 ml), and the extracts are combined and concentrated under reduced pressure to give the residue (4.06 g). The residue is purified by column chromatography (solvent; toluene:ethyl acetate=5:3) to give the following compounds.

4R(+)-hydroxy-2-(6-methoxycarbonyl-3-hexynyl)-2-cyclopentenone (1.25 g)

$[\alpha]_D^{20}$+17 9° (c=1, CHCl$_3$) (96.7% e.e.).

4S(−)-acetoxy-2-(6-methoxycarbonyl-3-hexynyl)-2-cyclopentenone (2.57 g)

$[\alpha]_D^{20}$−28.7° (c=1, CHCl$_3$).

A mixture of 4R(+)-hydroxy-2-(6-methoxycarbonyl-3-hexynyl)-2-cyclopentenone (1.18 g), a Lindlar catalyst (5% Pd-BaSO$_4$) (60 mg), quinoline (3 g) and isopropyl alcohol (10 ml) is charged to an atmospheric hydrogenation apparatus, and subjected to reduction at room temperature under atmospheric pressure. The reaction is completed in one hour. After completion of the reaction, the catalyst is removed by filtration and concentrated. The resulting residue is purified by silica gel column chromatography to give 4R(+)-hydroxy-2-(6-methoxycarbonyl-3-cis-hexenyl)-2-cyclopentenone (1.14 g, yield; 94%).

$[\alpha]_D^{20}$+19.2° (c=1, CHCl$_3$) (96.7% e.e.).

EXAMPLE 9

A mixture (9.45 g) of the compound [IX-1] and the racemic 4-hydroxycyclopentenone obtained in Example 7, chloral (0.24 g) and triethylamine (0.43 g) is reacted at 60° C. for 5 hours. After completion of the reaction, to the mixture are added methyl isobutyl ketone (30 ml) and water (20 ml). The organic layer is separated and washed successively with 1% aqueous hydrochloric acid solution and water, and methyl isobutyl ketone is distilled off therefrom to give 4-hydroxy-2-(6-methoxycarbonyl-3-hexynyl)-2-cyclopentenone (racemic 4-hydroxycyclopentenone) (8.13 g, yield; 86%).

$n_D^{25}$1.5000.

Subsequently, to a mixture of the above compound (7.09 g, 0.03 mole), dichloromethane (15 ml) and pyridine (15 ml) is added acetyl chloride (3.06 g, 0.039 mole) at 10 −15° C. over period of one hour. The reaction mixture is kept at the same temperature for 3 hours, and poured into ice-water. To the mixture is added dichloromethane (30 ml), and the organic layer is washed successively with 5% aqueous hydrochloric acid solution and water and concentrated to give 4-acetoxy-2-(6-methoxycarbonyl-3-hexynyl)-2-cyclopentenone [XI-1] (8.1 g, yield; 97%).

4-Acetoxy-2-(6-methoxycarbonyl-3-hexynyl)-2-cyclopentenone [XI-1] (4.17 g), chloroform (3 ml), Pseudomonas Lipase (AMANO "P") (200 mg) and 0.2 M phosphate buffer (pH 7.5, 50 ml) are charged in a flask and the mixture is vigorously stirred at 25°–30° C. for 8 hours. After completion of the reaction, the reaction solution is extracted twice with methyl isobutyl ketone (40 ml), and the extracts are combined and concentrated under reduced pressure to give the residue (4.15 g). The residue is purified by silica gel column chromatography (solvent; toluene:ethyl acetate=5:3) to give the following compounds.

4R(+)-hydroxy-2-(6-methoxycarbonyl-3-hexynyl)-2-cyclopentenone [I-1] (1.02 g)

$[\alpha]_D^{20}$+17.8° (c=1, CHCl$_3$) (96.4% e.e.).

4S(−)-acetoxy-2-(6-methoxycarbonyl-3-hexynyl)-2-cyclopentenone (2.70 g)

$[\alpha]_D^{20}$−25.7° (c=1, CHCl$_3$).

A mixture of 4R(+)-hydroxy-2-(6-methoxycarbonyl-3-hexynyl)-2-cyclopentenone [I-1] (1.18 g), a Lindlar catalyst (5% Pd-CaCO$_3$-PbO) (70 mg), cyclohexene (0.5 g) and ethyl acetate (30 ml) is charged in an atmospheric hydrogenation apparatus and subjected to reduction at room temperature under atmospheric pressure. The reduction is completed in 1.5 hour. After completion of the reaction, the catalyst is removed by filtration, and the filtrate is concentrated. The resulting residue is purified by silica gel column chromatography to give 4R(+)-hydroxy-2-(6-methoxycarbonyl-3-cis-hexenyl)-2-cyclopentenone (1.14 g, yield: 95.5%).

$[\alpha]_D^{20}$+19.1° (c=1, CHCl$_3$), (96.4% e.e.).

EXAMPLE 10

To a mixture of 6-methoxycarbonyl-1-carboxy-3-hexyne [VI-1] (27.6 g, 0.15 mole), furan (30 7 g, 0.45 mole) and dichloromethane (150 ml) is added trifluoroacetic anhydride (37.8 g, 0.18 mole) at room temperature, and the mixture is reacted at 30°–35° C. for 24 hours. After completion of the reaction, the reaction solution is poured into ice-water, and neutralized with 20% aqueous sodium hydroxide solution. The organic layer is separated and washed successively with 5% aqueous sodium hydrogen carbonate solution and water. The organic layer is concentrated under reduced pressure to give 1-oxo-1-furyl-7-methoxycarbonyl-4-heptyne [VII-1] (32.3 g, yield; 92%).

$n_D^{25}$ 1.5164.

To a mixture of the compound [VII-1] (30.4 g, 0.13 mole) obtained above, methanol (150 ml) and 28% solution (1.5 g) of sodium methylate in methanol is added sodium borohydride (2.46 g, 0.065 mole) at 5° C. The reaction mixture is reacted at the same temperature for 3 hours, and further at 10°–15° C. for 2 hours. After completion of the reaction, the reaction solution is poured into ice-water, and extracted with toluene. The organic layer is separated, washed with water and concentrated to give 1-hydroxy-1-furyl-7-methoxycarbonyl-4-heptyne [VIII-1] (29.2 g, yield; 95%).

$n_D^{25}$ 1.5082.

To the compound [VIII-1] (28.3 g, 0.12 mole) are added water (1200 g) and acetic acid (1.5 g), and the pH value thereof is adjusted to pH 4.4 with 5% aqueous sodium hydroxide solution. The mixture is heated with stirring at 100° C. for 25 hours. After completion of the reaction, the reaction solution is cooled and extracted twice with methyl isobutyl ketone (300 ml) and separated. Methyl isobutyl ketone is distilled off from the organic layer to give a mixture (21.5 g, yield; 76%) of 4-hydroxy-2-(6-methoxycarbonyl-3-hexynyl)-2-cyclopentenone (racemic 4-hydroxycyclopentenone) and 3-hydroxy-2-(6-methoxycarbonyl-3-hexynyl)-2-cyclopentenone [IX-1] (ratio thereof=6:4).

The mixture of a mixture (9.45 g, 0.04 mole) of the compound [IX-1] and the racemic 4-hydroxycyclopentenone, acetic acid (14 g), acetic anhydride (4 g) and sodium acetate (0.2 g) is reacted at 115°–120° C. for 4 hours. The reaction mixture is checked by gas chromatography, and when the starting materials are not detected, and the reaction is completed.

The reaction mixture is concentrated under reduced pressure, and to the residue are added toluene (100 ml) and water (50 ml). The organic layer is separated and washed successively with 8% aqueous sodium hydrogen carbonate solution and water. The organic layer is dried over anhydrous magnesium sulfate and concentrated to give 4-acetoxy-2-(6-methoxycarbonyl-3-hexynyl)-2-cyclopentenone [XI-1] (10.5 g, yield; 94.5%), b.p. 170°–175° C./0.5–0.6 mmHg.

A mixture of the compound [XI-1] (4.17 g) obtained above, a Lindlar catalyst (5% Pd-CaCO₃-PbO) (200 mg), cyclohexene (4 g) and toluene (20 ml) is charged in an atmospheric hydrogenation apparatus, and subjected to reduction at room temperature under atmospheric pressure. After completion of the reaction, the catalyst is removed by filtration, and the filtrate is concentrated. The resulting residue is purified by silica gel column chromatography to give 4-acetoxy-2-(6-methoxycarbonyl-3-cis-hexenyl)-2-cyclopentenone [XI-2] (3.95 g, yield; 94%).

4-Acetoxy-2-(6-methoxycarbonyl-3-cis-hexenyl)-2-cyclopentenone (2.80 g), dichloromethane (2 ml), Arthrobacter Lipase (manufactured by Shin-Nippon Kagaku K.K.) (40 mg) and 0.2 M phosphate buffer (pH 6.5, 50 ml) are charged in a flask, and the mixture is vigorously stirred at 35°–40° C. for 15 hours. After completion of the reaction, the reaction solution is extracted twice with methyl isobutyl ketone (40 ml). The extracts are combined and concentrated under reduced pressure to give the residue (2.75 g). The residue is purified by column chromatography (solvent; toluene:ethyl acetate=5:3) to give the following compounds.

4R(+)-hydroxy-2-(6-methoxycarbonyl-3-cis-hexenyl)-2-cyclopentenone (0.6 g)
$[\alpha]_D^{20}$ +17.2° (c=1, CHCl₃) (91.8% e.e.).
4S(−)-acetoxy-2-(6-methoxycarbonyl-3-cis-hexenyl)-2-cyclopentenone (1.97 g)
$[\alpha]_D^{20}$ −31.6° (c=1, CHCl₃).

EXAMPLE 11

A mixture of 6-methoxycarbonyl-1-carboxy-3-hexyne [VI-1] (18.4 g, 0.1 mole), furan (13.6 g, 0.2 mole), dichloroacetic anhydride (28.8 g, 0.12 mole), boron trifluoride ether complex (3.2 g) and toluene (100 ml) is reacted at 20°–30° C. for 10 hours. After completion of the reaction, the reaction mixture is cooled, and washed successively with water, 5% aqueous sodium carbonate solution and water, and the organic layer is dried over anhydrous magnesium sulfate and concentrated under reduced pressure. The resulting residue is purified by silica gel column chromatography to give 1-oxo-1-furyl-7-methoxycarbonyl-4-heptyne [VII-1] (15.2 g, yield; 65%), b.p. 120°–125° C./0.3 mmHg.

A mixture of the compound [VII-1] (14.1 g, 0.06 mole) obtained above, sodium trimethoxyborohydride (10 g, 0.078 mole) and dimethoxyethane (100 ml) is stirred at room temperature. After confirming the disappearance of the starting materials, the reaction mixture is poured into ice-water, and extracted twice with ethyl acetate (100 ml). The organic layer is washed with water and concentrated to give 1-hydroxy-1-furyl-7-methoxycarbonyl-4-heptyne [VIII-1] (13.7 g, yield; 96.5%).

To the compound [VIII-1] (11.8 g, 0.05 mole) is added a buffer (pH 4.2) consisting of water (500 g), dipotassium hydrogen phosphate (0.3 g) and phosphoric acid, and the mixture is heated with stirring at 100° C. under nitrogen atmosphere until the starting materials are consumed. In the reaction mixture, there is obtained a mixture of 3-hydroxy-2-(6-methoxycarbonyl-3-hexynyl)-4-cyclopentenone [IX-1] and 4-hydroxy-2-(6-methoxycarbonyl-3-hexynyl)-2-cyclopentenone (racemic 4-hydroxycyclopentenone). The reaction mixture is cooled, and the pH value thereof is adjusted to pH 7.6 with 1 N aqueous potassium hydroxide solution. The mixture is heated with stirring at 100° C. under nitrogen atmosphere until the above 3-hydroxy-2-(6-methoxycarbonyl-3-hexynyl)-4-cyclopentenone [IX-1] is consumed. After completion of the reaction, the reaction mixture is cooled and extracted twice with methyl isobutyl ketone (600 g). The organic layer is separated and methyl isobutyl ketone is distilled off therefrom to give 4-hydroxy-2-(6-methoxycarbonyl-3-hexynyl)-2-cyclopentenone (racemic 4-hydroxycyclopentenone) (8.1 g, yield; 69%).

4-Hydroxy-2-(6-methoxycarbonyl-3-hexynyl)-2-cyclopentenone (4.72 g), a Lindlar catalyst (5% Pd-CaCO₃-PbO) (200 mg), cyclohexene (4 g) and toluene (50 ml) are charged in an atmospheric hydrogenation apparatus and subjected to reduction at room temperature under atmospheric pressure. The reaction is completed in one hour. After completion of the reaction, the catalyst is removed by filtration and concentrated. The resulting residue is purified by silica gel column chromatography to give 4-hydroxy-2-(6-methoxycarbonyl-3-cis-hexenyl)-2-cyclopentenone (4.5 g, yield; 94.5%). $n_D^{25}$ 1.5023.

A mixture of the above compound (3.57 g, 0.015 mole), acetic anhydride (4.59 g, 0.03 mole), conc. sulfuric acid (0.05 g) and methyl isobutyl ketone (10 ml) is stirred at 40° C. for 3.5 hours. After completion of the reaction, the reaction mixture is cooled and poured into ice-water and extracted with methyl isobutyl ketone (20 ml). The organic layer is washed successively with 5% aqueous sodium hydrogen carbonate solution and water, and concentrated to give 4-acetoxy-2-(6-methoxycarbonyl-3-cis-hexenyl)-2-cyclopentenone [XI-2] (4.03 g, yield; 96.5%).

The compound [XI-2] (2.78 g) obtained above, Arthrobacter Lipase (manufactured by Shin-Nippon Kagaku K.K.) (50 mg) and 0.2 M phosphate buffer (pH 7.0, 30 ml) are charged in a flask, and the mixture is stirred at 25°–30° C. for 7 hours. After completion of the reaction, the reaction solution is extracted twice with methyl isobutyl ketone (20 ml), and the extracts are combined and concentrated under reduced pressure to give the residue (2.68 g), which is purified by column chromatography (solvent; toluene:ethyl acetate=5:3) to give the following compounds.

4R(+)-hydroxy-2-(6-methoxycarbonyl-3-cis-hexenyl)-2-cyclopentenone [I-2] (0.67 g)
$[\alpha]_D^{20}$ +17° (c=1, CHCl₃) (90.7% e.e.).
4S(−)-acetoxy-2-(6-methoxycarbonyl-3-cis-hexenyl)-2-cyclopentenone (1.89 g)
$[\alpha]_D^{20}$ −30.9° (c=1, CHCl₃).

EXAMPLE 12

A mixture of the mixture (9.45 g) of the compound [IX-1] and the racemic 4-hydroxycyclopentenone obtained in Example 10, chloral (0.24 g) and triethylamine (0.43 g) is reacted at 60° C. for 5 hours. After completion of the reaction, to the mixture are added methyl isobutyl ketone (30 ml) and water (20 ml). The organic layer is separated and washed successively with 1% aqueous hydrochloric acid solution and water, and methyl isobutyl ketone is distilled off therefrom to give 4-hydroxy-2-(6-methoxycarbonyl-3-hexynyl)-2-cyclopentenone (8.13 g, yield; 86%).

To the above compound (7.09 g, 0.03 mole) are added dichloromethane (15 ml) and pyridine (15 ml), and to the mixture is added acetyl chloride (3.06 g, 0.039 mole) at 10°-15° C. over a period of one hour. The mixture is kept at the same temperature for 3 hours, and poured into ice-water and thereto is added dichloromethane (30 ml). The organic layer is washed successively with 5% aqueous hydrochloric acid solution and water, and concentrated to give 4-acetoxy-2-(6-methoxycarbonyl-3-hexynyl)-2-cyclopentenone [XI-1] (8.1 g, yield; 97%).

4-Acetoxy-2-(6-methoxycarbonyl-3-hexynyl)-2-cyclopentenone [XI-1] (4.17 g), a Lindlar catalyst (5% Pd-BaSO$_4$) (150 mg), quinoline (6 g) and isopropyl alcohol (20 ml) are charged in an atmospheric hydrogenation apparatus and subjected to reduction at room temperature under atmospheric pressure. The reaction is completed in 15 hours. After completion of the reaction, the catalyst is removed by filtration and the filtrate is concentrated. The resulting residue is purified by silica gel column chromatography to give 4-acetoxy-2-(6-methoxycarbonyl-3-cis-hexenyl)-2-cyclopentenone [XI-2] (3.99 g, yield; 95%).

4-Acetoxy-2-(6-methoxycarbonyl-3-cis-hexenyl)-2-cyclopentenone [XI-2] (2.80 g) obtained above, toluene (2 ml), Pseudomonas Lipase (AMANO "P") (80 mg) and 0.2 M phosphate buffer (pH 6.5, 50 ml) are charged in a flask, and the mixture is vigorously stirred at 25°-30° C. for 6 hours. After completion of the reaction, the reaction solution is extracted twice with methyl isobutyl ketone (30 ml), and the extracts are combined and concentrated under reduced pressure to give the residue (2.71 g). The residue is purified by column chromatography (solvent; toluene:ethyl acetate=5:3) to give the following compounds.

4R(+)-hydroxy-2-(6-methoxycarbonyl-3-cis-hexenyl)-2-cyclopentenone [I-2] (0.64 g)
$[\alpha]_D^{20}$ +16.8° (c=1, CHCl$_3$) (89.4% e.e.).
4S(−)-acetoxy-2-(6-methoxycarbonyl-3-cis-hexenyl)-2-cyclopentenone (1.74 g)
$[\alpha]_D^{20}$ −29.9° (c=1, CHCl$_3$).

EXAMPLE 13

To a mixture of 6-methoxycarbonyl-1-carboxy-3-hexyne [VI-1] (27.6 g, 0.15 mole), furan (30.7 g, 0.45 mole) and dichloromethane (150 ml) is added trifluoroacetic anhydride (37.8 g, 0.18 mole) at room temperature, and the mixture is reacted at 30°-35° C. for 24 hours. After completion of the reaction, the reaction solution is poured into ice-water and neutralized with 20% aqueous sodium hydroxide solution. The organic layer is separated and washed successively with 5% aqueous sodium hydrogen carbonate solution and water. The organic layer is concentrated under reduced pressure to give 1-oxo-1-furyl-7-methoxycarbonyl-4-heptyne [VII-1] (32.3 g, yield; 92%).

To a mixture of the compound [VII-1] (30.4 g, 0.13 mole) obtained above, methanol (150 ml) and 28% solution (1.5 g) of sodium methylate in methanol is added sodium borohydride (2.46 g, 0.065 mole) at 5° C. The reaction mixture is reacted at the same temperature for 3 hours, and further at 10°-15° C. for 2 hours. After completion of the reaction, the reaction mixture is poured into ice-water and extracted with toluene. The organic layer is separated, washed with water and concentrated to give 1-hydroxy-1-furyl-7-methoxycarbonyl-4-heptyne [VIII-1] (29.2 g, yield; 95%).

To the compound [VIII-1] (28.3 g, 0.12 mole) are added water (1200 g) and acetic acid (1.5 g), and the pH value thereof is adjusted to pH 4.4 with 5% aqueous sodium hydroxide solution. The mixture is heated with stirring at 100° C. for 25 hours. After completion of the reaction, the reaction mixture is cooled, extracted twice with methyl isobutyl ketone (300 ml) and separated. Methyl isobutyl ketone is distilled off from the organic layer to give a mixture (21.5 g, yield; 76%) of 4-hydroxy-2-(6-methoxycarbonyl-3-hexynyl)-2-cyclopentenone (racemic 4-hydroxycyclopentenone) and 3-hydroxy-2-(6-methoxycarbonyl-3-hexynyl)-2-cyclopentenone [IX-1] (ratio thereof=6:4).

A mixture of the mixture (9.45 g, 0.04 mole) of the compound [IX-1] and the racemic 4-hydroxycyclopentenone obtained above, acetic acid (14 g), acetic anhydride (4 g) and sodium acetate (0.2 g) is reacted at 115°-120° C. for 4 hours. The reaction mixture is checked by gas chromatography, and when the starting materials are not detected therein, the reaction is completed. The reaction mixture is concentrated under reduced pressure, and to the resulting residue are added toluene (100 ml) and water (50 ml). The organic layer is separated, washed successively with 8% aqueous sodium hydrogen carbonate solution and water, dried over anhydrous magnesium sulfate and concentrated to give 4-acetoxy-2-(6-methoxycarbonyl-3-hexynyl)-2-cyclopentenone [XI-1] (10.5 g, yield; 94.5%), b.p. 170°-175° C./0.5-0.6 mmHg.

To the compound [XI-1] (5.56 g) are added methanol (20 g) and 35% aqueous hydrochloric acid solution (1.1 g), and the mixture is reacted at 40°-45° C. for 4 hours. After completion of the reaction, the reaction mixture is cooled to below 10° C., and the pH value thereof is adjusted to pH 4.0 with 10% aqueous sodium hydroxide solution, Methanol is distilled off therefrom, and the resulting residue is extracted with methyl isobutyl ketone (30 ml), and washed with water. The organic layer is concentrated under reduced pressure and the resulting residue is purified by column chromatography (solvent; toluene : ethyl acetate=5:3) to give 4-hydroxy-2-(6-methoxycarbonyl-3-hexynyl)-2-cyclopentenone (4.48 g, yield; 94.8%).

EXAMPLE 14

A mixture of the compound [XI-1] (2.78 g) obtained in Example 13, 70% sulfuric acid (1 g) and methanol (15 g) is reacted at 30° C. for 6 hours. After completion of the reaction, the mixture is treated in the same manner as in Example 13, and further purified to give 4-hydroxy-2-(6-methoxycarbonyl-3-hexynyl)-2-cyclopentenone (2.28 g, yield; 96.5%).

EXAMPLE 15

A mixture of 6-methoxycarbonyl-1-carboxy-3-hexyne [VI-1] (18.4 g, 0.1 mole), furan (13.6 g, 0.2 mole), dichloroacetic anhydride (28.8 g, 0.12 mole), boron trifluoride ether complex (3.2 g) and toluene (100 ml) is reacted at 20°-30° C. for 10 hours. After completion of the reaction, the reaction mixture is cooled, washed successively with water, 5% aqueous sodium carbonate solution and water, and the organic layer is dried over anhydrous magnesium sulfate. The dried organic layer is concentrated under reduced pressure, and the resulting residue is purified by silica gel column chromatography to give 1-oxo-1-furyl-7-methoxycarbonyl-4-heptyne [VII-1] (15.2 g, yield; 65%), b.p. 120°–125° C./0.8 mmHg.

A mixture of the compound [VII-1] (14.1 g, 0.06 mole) obtained above, sodium trimethoxyborohydride (10 g, 0.078 mole) and dimethoxyethane (100 ml) is stirred at room temperature. After confirming the disappearance of the starting materials, the reaction mixture is poured into ice-water and extracted twice with ethyl acetate (100 ml). The organic layer is washed with water, and concentrated to give 1-hydroxy-1-furyl-7-methoxycarbonyl-4-heptyne [VIII-1] (13.7 g, yield; 96.5%).

The compound [VIII-1] (11.8 g, 0.05 mole) obtained above and a buffer solution (pH 4.2) consisting of water (500 g), dipotassium hydrogen phosphate (0.3 g) and phosphoric acid are charged in a flask, and the mixture is heated with stirring at 100° C. under nitrogen atmosphere until the starting materials are consumed. In the reaction mixture, there is obtained a mixture of 3-hydroxy-2-(6-methoxycarbonyl-3-hexynyl)-4-cyclopentenone [IX-1] and 4-hydroxy-2-(6-methoxycarbonyl-3-hexynyl)-2-cyclopentenone (racemic 4-hydroxycyclopentenone). The reaction mixture is cooled and the pH value thereof is adjusted to pH 7.6 with 1 N aqueous potassium hydroxide solution. The mixture is heated with stirring at 100° C. under nitrogen atmosphere until 3-hydroxy-2-(6-methoxycarbonyl-3-hexynyl)-4-cyclopentenone [IX-1] produced above is consumed. After completion of the reaction, the reaction mixture is cooled and extracted twice with methyl isobutyl ketone (600 g). The organic layer is separated, and methyl isobutyl ketone is distilled off therefrom to give 4-hydroxy-2-(6-methoxycarbonyl-3-hexynyl)-2-cyclopentenone (racemic 4-hydroxycyclopentenone) (8.1 g, yield; 69%).

EXAMPLE 16

A mixture of the mixture (9.45 g) of the compound [IX-1] and the racemic 4-hydroxycyclopentenone obtained in Example 13, chloral (0.24 g) and triethylamine (0.43 g) is reacted at 60° C. for 5 hours. After completion of the reaction, to the mixture are added methyl isobutyl ketone (30 ml) and water (20 ml), and the organic layer is separated, washed successively with 1% aqueous hydrochloric acid solution and water, and methyl isobutyl ketone is distilled off therefrom to give 4-hydroxy-2-(6-methoxycarbonyl-3-hexynyl)-2-cyclopentenone [racemic 4-hydroxycyclopentenone) (8.13 g, yield; 86%).

EXAMPLE 17

To a mixture of 6-methoxycarbonyl-1-carboxy-3-hexyne [VI-1] (27.6 g, 0.15 mole), furan (30.7 g, 0.45 mole) and dichloromethane (150 ml) is added trifluoroacetic anhydride (37.8 g, 0.18 mole) at room temperature, and the mixture is reacted at 30°–35° C. for 24 hours. After completion of the reaction, the reaction solution is poured into ice-water, and neutralized with 20% aqueous sodium hydroxide solution. The organic layer is separated and washed successively with 5% aqueous sodium hydrogen carbonate solution and water, and concentrated under reduced pressure to give 1-oxo-1-furyl-7-methoxycarbonyl-4-heptyne [VII-1] (32.3 g, yield; 92%).

To a mixture of the compound [VII-1] (30.4 g, 0.13 mole) obtained above, methanol (150 ml) and 28% solution (1.5 g) of sodium methylate in methanol is added sodium borohydride (2.46 g, 0.065 mole) at 5° C. The mixture is reacted at the same temperature for 3 hours, and further at 10°–15° C. for 2 hours. After completion of the reaction, the reaction solution is poured into ice-water, and extracted with toluene. The organic layer is separated and washed with water, and concentrated to give 1-hydroxy-1-furyl-7-methoxycarbonyl-4-heptyne [VIII-1] (29.2 g, yield; 95%).

To the compound [VIII-1] (28.3 g, 0.12 mole) obtained above are added water (1200 g) and acetic acid (1.5 g), and the pH value thereof is adjusted to pH 3.2 with 5% sodium hydroxide solution. The mixture is heated with stirring at 90° C. for 12 hours. After completion of the reaction, the reaction solution is cooled, extracted twice with methyl isobutyl ketone (300 ml) and separated. Methyl isobutyl ketone is distilled off from the organic layer to give 3-hydroxy-2-(6-methoxycarbonyl-3-hexynyl)-2-cyclopentenone [IX-1] (19.5 g, yield; 69%).

EXAMPLE 18

A mixture of the compound [IX-1] (5.12 g) obtained in Example 17, chloral (0.33 g) and triethylamine (0.58 g) is reacted at 60° C. for 8 hours. After completion of the reaction, to the mixture are added methyl isobutyl ketone (20 ml) and water (15 ml). The organic layer is separated and washed successively with 1% aqueous hydrochloric acid solution and water, and methyl isobutyl ketone is distilled off therefrom to give 4-hydroxy-2-(6-methoxycarbonyl-3-hexynyl)-2-cyclopentenone (racemic 4-hydroxycyclopentenone) (4.66 g, yield; 91%).

EXAMPLE 19

A mixture of 1,6-dicarbomethoxy-3-hexyne [II-1] (5 g), a Lindlar catalyst (5% Pd-CaCO₃-PbO) (50 mg), quinoline (25 mg) and methanol (15 ml) is charged in an atmospheric hydrogenation apparatus and subjected to reduction at room temperature under atmospheric pressure. After completion of the reaction, the catalyst is removed by filtration and the filtrate is concentrated to give 1,6-dicarbomethoxy-cis-3-hexene [II-2] (4.70 g, yield; 93.0%), b.p. 92°–95° C./0.3 mmHg.

EXAMPLE 20

The compound [II-2] (75.7 g) obtained in Example 19 is dissolved in methanol (30 g) and the mixture is cooled to 5° C. To the mixture is added 15% solution (216 g) of anhydrous barium hydroxide in methanol, and the mixture is stirred. After 17 hours, the reaction mixture is filtered, and the filtrate is dried under reduced pressure to give a crystalline product (66.8 g). The product is suspended in 1,2-dichloroethane (330 g) and to the suspension are added 10% hydrochloric acid (115 g) and water (200 g), and the temperature thereof is raised to 40°–45° C. The mixture is stirred for 2 hours, and separated. The organic layer is washed with water (200 g) and concentrated under reduced pressure to give 6-methoxycarbonyl-1-carboxy-cis-3-hexene [VI-2] (32.2 g, yield; 45.7%), b.p. 118°–124° C./0.2 mmHg.

To a mixture of the compound [VI-2] (25.1 g), furan (13.8 g, 0.20 mole) and chloroform (100 ml) is added trifluoroacetic anhydride (15.5 g, 0.074 mole) at room temperature, and the mixture is reacted at 20°–25° C. for 24 hours. After completion of the reaction, the reaction solution is poured into 5% aqueous sodium carbonate solution (200 ml). The organic layer is separated, washed with water and concentrated to give 1-oxo-1- furyl-7-methoxy-carbonyl-cis-4-heptene [VII-2] (14.5 g, yield; 91%).

The compound [VII-2] (12.8 g, 0.054 mole) obtained above is dissolved in a mixture of methanol (100 ml) and chloroform (50 ml), and thereto is added sodium borohydride (20.4 g, 0.054 mole) at 10°-20° C. The mixture is kept at the same temperature for 2 hours, and poured into ice-water and extracted with toluene. The organic layer is separated, washed with water and concentrated to give 1-hydroxy-1-furyl-7-methoxycarbonyl-4-heptene [VIII-2] (12.3 g, yield; 96%).

To the compound [VIII-2] (11.3 g, 0.047 mole) are added water (473 g) and acetic acid (0.34 g), and the pH value thereof is adjusted to pH 4.3 with 5% aqueous potassium hydroxide solution. The mixture is heated with stirring at 100° C. until the starting materials are consumed. In the reaction mixture, there is obtained a mixture of 4-hydroxy-2-(6-methoxycarbonyl-3-cis-hexenyl)-2-cyclopentenone (racemic 4-hydroxycyclopentenone) and 3-hydroxy-2-(6-methoxycarbonyl-3-cis-hexenyl)-2-cyclopentenone [IX-2] (ratio thereof=65:35). The pH value of the reaction mixture is raised to pH 7.0 and the mixture is reacted for further 10 hours until the compound [IX-2] is consumed. After completion of the reaction, the reaction mixture is extracted twice with ethyl acetate (300 ml). The extract is concentrated and the resulting residue is purified by column chromatography (solvent; toluene:ethyl acetate=5:3) to give 4-hydroxy-2-(6-methoxycarbonyl-3-cis-hexenyl)-2-cyclopentenone (racemic 4-hydroxycyclopentenone) (7.97 g, yield; 71%).

$n_D^{25}$ 1.5023.

A mixture of the above compound (7.14 g, 0.03 mole), acetic anhydride (9.18 g, 0.06 mole), conc. sulfuric acid (0.1 g) and methyl isobutyl ketone (20 ml) is stirred at 40° C. for 3.5 hours. After completion of the reaction, the reaction mixture is cooled and poured into ice-water, and then extracted with methyl isobutyl ketone (40 ml). The organic layer is washed successively with 5% aqueous sodium hydrogen carbonate solution and water, and concentrated to give 4-acetoxy-2-(6-methoxycarbonyl-3-cis-hexenyl)-2-cyclopentenone [XI-2] (8.06 g, yield; 96.5%).

The compound [XI-2] (5.56 g), Arthrobacter Lipase (manufactured by Shin-Nippon Kagaku K.K.) (100 mg) and 0.2 M phosphate buffer (pH 7.0, 60 ml) are charged in a flask, and the mixture is stirred at 25°-30° C. for 7 hours. After completion of the reaction, the reaction mixture is extracted twice with methyl isobutyl ketone (40 ml), and the extracts are combined and concentrated under reduced pressure to give the residue (5.36 g), which is purified by column chromatography (solvent; toluene:ethyl acetate=5:3) to give the following compounds.

4R(+)-hydroxy-2-(6-methoxycarbonyl-3-cis-hexenyl)2-cyclopentenone [I-2] (1.34 g).

$[\alpha]_D^{20}$ +17.3° (c=1, CHCl$_3$) (92.3% e.e.).

4S(−)-acetoxy-2-(6-methoxycarbonyl-3-cis-hexenyl)-2-cyclopentenone (3.78 g)

$[\alpha]_D^{20}$ −30.8° (c=1, CHCl$_3$).

EXAMPLE 21

A mixture of 6-methoxycarbonyl-1-carboxy-3-hexyne [VI-1] (4.0 g), a Lindlar catalyst (5% Pd-BaSO$_4$) (40 mg), quinoline (80 mg) and methanol (12 ml) is charged in an atmospheric hydrogenation apparatus and subjected to reduction at room temperature under atmospheric pressure. After completion of the reaction, the catalyst is removed by filtration and the filtrate is concentrated. The resulting residue is dissolved in toluene (20 ml) and washed successively with 5% aqueous hydrochloric acid solution and water. The organic layer is dried over anhydrous magnesium sulfate, filtered and concentrated to give 6-methoxycarbonyl-1-carboxy-cis-3-hexene [VI-2] (3.38 g, yield; 83.7 %), b.p. 118°-124° C./0.2 mmHg.

EXAMPLE 22

A mixture of 1-oxo-1-furyl-7-methoxycarbonyl-4-heptyne [VII-1] (3.0 g) obtained in Example 13, a Lindlar catalyst (5% Pd-CaCO$_3$-PbO) (30 mg), cyclohexene (5.26 g) and toluene (12 ml) is charged in an atmospheric hydrogenation apparatus and subjected to reduction at room temperature under atmospheric pressure. After completion of the reaction, the catalyst is removed by filtration and the filtrate is concentrated to give 1-oxo-1-furyl-7-methoxycarbony-cis-4-heptene [VII-2] (2.74 g, yield; 90.4%).

$n_D^{25}$ 1.5096.

The compound [VII-2] obtained above is treated in the same manner as in Example 20 to give 4R(+)-hydroxy-2-(6-methoxycarbonyl-cis-3-hexenyl)-2-cyclopentenone (racemic 4-hydroxycyclopentenone).

EXAMPLE 23

A mixture of 1-hydroxy-1-furyl-7-methoxycarbonyl-4-heptyne [VIII-1] (4.23 g) obtained in Example 13, a Lindlar catalyst (5% Pd-CaCO$_3$-PbO) (42 mg), cyclohexene (4.41 g) and toluene (21 ml) is charged in an atmospheric hydrogenation apparatus and subjected to reduction at room temperature under atmospheric pressure. After completion of the reaction, the catalyst is removed by filtration and the 1 filtrate is concentrated to give 1-hydroxy-1-furyl-7-methoxycarbony-cis-4-heptene [VIII-2] (3.77 g, yield; 88.3%).

$n_D^{25}$ 1.4937.

To the compound [VIII-2] (2.50 g) obtained above are added water (123.8 g) and acetic acid (0.19 g), and the pH value of the mixture is adjusted to pH 4.2 with 5% aqueous sodium hydroxide solution and the mixture is heated with stirring at 100° C. for 26 hours. After completion of the reaction, the reaction mixture is cooled and extracted twice with methyl isobutyl ketone (50 ml). The organic layer is separated and concentrated to give a mixture (1.78 g, yield; 71%) of 4-hydroxy-2-(6-methoxycarbonyl-cis-3-hexenyl)-2-cyclopentenone (racemic 4-hydroxycyclopentenone) and 3-hydroxy-2-(6-methoxycarbonyl-cis-3-hexenyl)-2-cyclopentenone [IX-2] (ratio thereof=4.9:5.1).

A mixture of the mixture (1.60 g) of the compound [IX-2] and the racemic 4-hydroxycyclopentenone obtained above, chloral (15 mg) and triethylamine (17 mg) is reacted at 60° C. for 5 hours. After completion of the reaction, to the mixture are added methyl isobutyl ketone (20 ml) and water (10 ml), and the organic layer is separated. The organic layer is washed successively with 1% aqueous hydrochloric acid solution and water, and methyl isobutyl ketone is distilled off from the organic layer to give 4-hydroxy-2-(6-methoxycarbonyl-cis-3-hexenyl)-2-cyclopentenone (racemic 4-hydroxycyclopentenone) (1.40 g, yield; 87.8%).

$n_D^{25}$ 1.5023.

What is claimed is:

1. A process for preparing optically active 4-hydroxycyclopentenones of the formula:

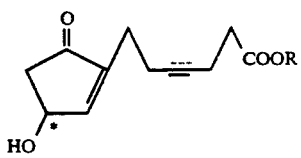     [I]

wherein R is a $C_1$–$C_6$ alkyl, the symbol ≡ means a double bond or a triple bond, and the * marked carbon is an asymmetric carbon, which comprises treating a cyclopentenone ester of the formula:

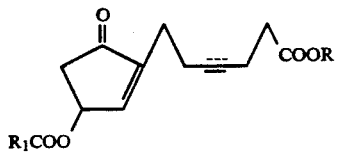     [XI]

wherein R, and the symbol ≡ are as defined above and $R_1$ is a $C_1$–$C_5$ alkyl optionally having a halogen substituent, with an esterase which can be preferentially hydrolyze either one of the optical forms of said ester [XI]; wherein the cyclopentenone ester [XI] is prepared by the steps of (a) reacting a diester of the formula:

     [II]

wherein R and the symbol ≡ are as defined above, with an alkaline earth metal hydroxide, followed by decomposing the product with an acid to give a half ester of the formula:

     [VI]

wherein R and the symbol ≡ are as defined above,
(b) reacting the half ester [VI] with furan in the presence of an acid anhydride of the formula:

     [XIII]
(XYCHCO)$_2$O wherein X and Y are the same or different and are each a hydrogen atom, a chlorine atom or a bromine atom, provided that both X and Y are not simultaneously a hydrogen atom, in the presence of a boron trifluoride or a boron trifluoride complex catalyst, or
reacting the half ester [VI] with furan in the presence of trifluoroacetic acid anhydride to give a furfuryl ketone of the formula:

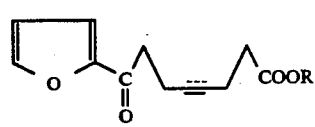     [VII]

wherein R and the symbol ≡ are as defined above,
(c) treating the furfuryl ketone [VII] with a reducing agent to give a furancarbinol of the formula:

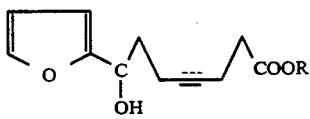     [VIII]

wherein R and the symbol ≡ are as defined above,
(d) treating the furancarbinol [VIII] in an aqueous solvent at pH 3.5–6 in the presence or absence of a catalyst to give a 3-hydroxycyclopentenone [IX]

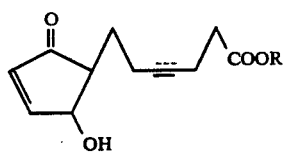     [IX]

or a racemic 4-hydroxycyclopentenone of the formula:

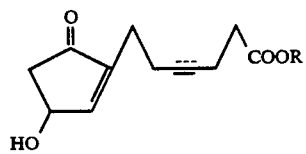

wherein R and the symbol ≡ are as defined above, and
(e) subjecting the 3-hydroxycyclopentenone [IX] or the racemic 4-hydroxycyclopentenone to
1-i) treatment in an aqueous solvent at pH 6–9, or treatment with chloral and an organic amine to convert into racemic 4-hydroxycyclopentenone, and then
1-ii) reacting the racemic 4-hydroxycyclopentenone with a carboxylic acid of the formula:

     [X]
$R_1$COOH wherein $R_1$ is as defined above, or a derivative thereof in the presence of a basic substance or acid substance, or
2) treatment with an aliphatic carboxylic acid of the formula:

     [X']
$R_1'$COOH wherein $R_1'$ is a $C_1$–$C_5$ alkyl optionally having a halogen substituent, an anhydride of the aliphatic carboxylic acid [X'] and a metal salt of the aliphatic carboxylic acid [X'].

2. The process according to claim 1, wherein a diester of the formula:

     [II-1]

wherein R is as defined in claim 1 is used as the starting diester [II] and the diester [II-1] is subjected to partial hydrogenation in the presence of a catalyst before the step (a) or after any step of a) to e) to give the optically active cyclopentenone [I] wherein the symbol χ is a double bond.

3. The process according to claim 1, wherein the optically active cyclopentenone [I] wherein the symbol χ is double bond is prepared by subjecting the produced optically active cyclopentenone of the formula:

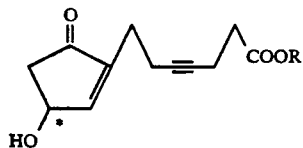
[I-1]

wherein R and the * marked carbon are as defined in claim 1, to partial hydrogenation in the presence of a catalyst.

4. The process according to claim 1, wherein the cyclopentenone ester [XI] is a compound of the formula [XI] wherein the symbol ≡ is a double bond, which is prepared by subjecting a compound of the formula:

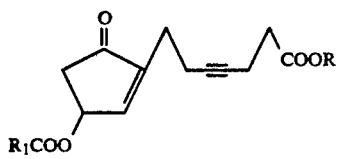
[XI-1]

wherein R and $R_1$ are as defined in claim 1, to partial hydrogenation in the presence of a catalyst.

5. The process according to claim 1, wherein the racemic 4-hydroxycyclopentenone having triple bond as the symbol ≡ is subjected to partial hydrogenation in the presence of a catalyst.

6. The process according to claim 1, wherein the starting diester [II] is a compound of the formula:

[II-1]

wherein R is as defined in claim 1, which is prepared by reacting an acetylene derivative of the formula:

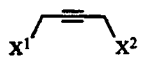
[III]

wherein $X^1$ and $X^2$ are each chlorine atom, bromine atom, iodine atom, methanesulfonyloxy, or p-toluenesulfonyloxy, with an acetoacetic acid ester of the formula:

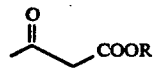
[IV]

wherein R is a $C_1$-$C_6$ alkyl, in the presence of a metal alkoxide.

7. A process for preparing 3-hydroxycyclopentenone [IX] and/or racemic 4-hydroxycyclopentenone of the formulae:

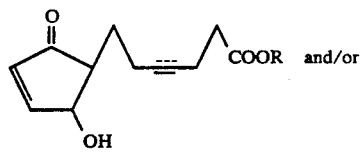
[IX]

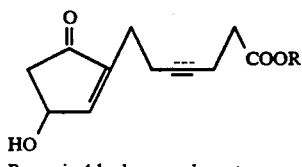
Racemic 4-hydroxycyclopentenone wherein R is a $C_1$-$C_6$ alkyl and the symbol ≡ means a double bond or triple bond, which comprises the steps of (a) reacting a diester of the formula:

[II]

wherein R and the symbol ≡ are as defined above, with an alkaline earth metal hydroxide, followed by decomposing the product with an acid to give a half ester of the formula:

[VI]

wherein R and the symbol ≡ are as defined above, (b) reacting the half ester [VI] with furan in the presence of an acid anhydride of the formula:

(XYCHCO)$_2$O                    [XIII]

wherein X and Y are the same or different and are each hydrogen atom, chlorine atom, or bromine atom, provided that both X and Y are not simultaneously hydrogen atom, in the presence of a boron trifluoride or boron trifluoride complex catalyst, or reacting the half ester [VI] with furan in the presence of trifluoroacetic acid anhydride to give a furfuryl ketone of the formula:

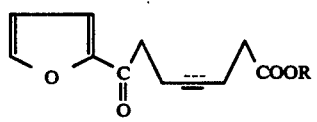
[VII]

wherein R and the symbol ≡ are as defined above, (c) treating the furfuryl ketone [VII] with a reducing agent to give a furancarbinol of the formula:

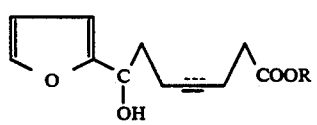
[VIII]

(d) treating the furancarbinol [VIII] in an aqueous solvent at pH 3.5-6 in the presence or absence of a catalyst, e) in case that the starting diester [II] has a triple bond as the symbol ≡ and the desired 3-hydroxycyclopentenone [IX] and/or racemic 4-hydroxycyclopentenone have a double bond as the symbol ≡ subjecting the product before the step (a) or after any step of a) to d) to partial hydrogenation in the presence of a catalyst.

8. The process according to claim 7, wherein the starting diester [II] is a compound of the formula:

  [II-1]

wherein R is as defined in claim 7, which is prepared by reacting an acetylene derivative of the formula:

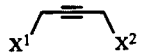  [III]

wherein $X^1$ and $X^2$ are each chlorine atom, bromine atom, iodine atom, methanesulfonyloxy, or p-toluenesulfonyloxy, with an acetoacetic acid ester of the formula:

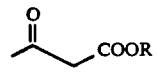  [IV]

wherein R is as defined in claim 7, in the presence of a metal alkoxide.

9. A process for preparing a racemic 4-hydroxycyclopentenone of the formula:

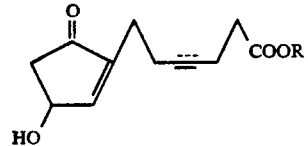

wherein R is a $C_1$-$C_6$ alkyl and the symbol ≡ means double bond or triple bond, which comprises the steps of (a) reacting a diester of the formula:

  [II]

wherein R and the symbol ≡ are as defined above, with an alkaline earth metal hydroxide, followed by decomposing the product with an acid to give a half ester of the formula:

  [VI]

wherein R and the symbol ≡ are as defined above,
(b) reacting the half ester [VI] with furan in the presence of an acid anhydride of the formula:

$(XYCHCO)_2O$  [XIII]

wherein X and Y are the same or different and are each hydrogen atom, chlorine atom, or bromine atom, provided that both X and Y are not simultaneously hydrogen atom, in the presence of a boron trifluoride or boron trifluoride complex catalyst, or reacting the half ester [VI] with furan in the presence of trifluoroacetic acid anhydride to give a furfuryl ketone of the formula:

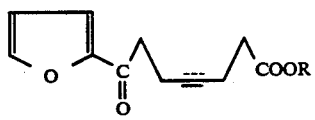  [VII]

wherein R and the symbol ≡ are as defined above,
(c) treating the furfuryl ketone [VII] with a reducing agent to give a furancarbinol of the formula:

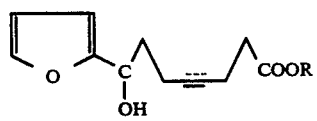  [VIII]

wherein R and the symbol ≡ are as defined above,
(d) treating the furancarbinol [VIII] in an aqueous solvent at pH 3.5-6 in the presence or absence of a catalyst to give a 3-hydroxycyclopentenone [IX] and/or racemic 4-hydroxycyclopentenone of the formulae:

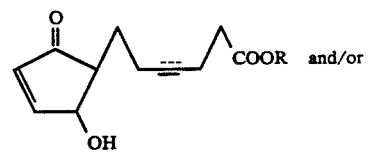 and/or

[IX]

Racemic 4-hydroxycyclopentenone wherein R and the symbol ≡ are as defined above,
(e) subjecting the 3-hydroxycyclopentenone [IX] and/or racemic 4-hydroxycyclopentenone to
1) treatment in an aqueous solvent at pH 6-9, or treatment with chloral and an organic amine to convert into racemic 4-hydroxycyclopentenone, or
2-i) treatment with an aliphatic carboxylic acid of the formula:

$R_1'COOH$  [X']

wherein $R_1'$ is a $C_1$-$C_5$ alkyl having optionally a halogen substituent, an anhydride of the aliphatic carboxylic acid [X'] and a metal salt of the aliphatic carboxylic acid [X'] to give a cyclopentenone ester of the formula:

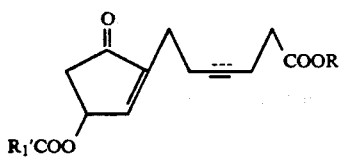

wherein R, R₁' and the symbol ⇌ are as defined above, and 2-ii) treating the cyclopentenone ester [XI] with an alcohol of the formula:

R—OH  [XII]

wherein R is as defined above, in the presence of an acid catalyst, and f) in case that the starting diester [II] has a triple bond as the symbol ⇌ and the desired racemic 4-hydroxycyclopentenone has a double bond as the symbol ⇌ subjecting the product before the step (a) or after any step of a) to e) to partial hydrogenation in the presence of a catalyst.

10. The process according to claim 9, wherein the starting diester [II] is a compound of the formula:

wherein R is as defined in claim 9, which is prepared by reacting an acetylene derivative of the formula:

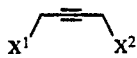

wherein $X^1$ and $X^2$ are each chlorine atom, bromine atom, iodine atom, methanesulfonyloxy, or p-toluenesulfonyloxy, with an acetoacetic acid ester of the formula:

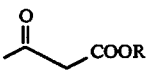

wherein R is as defined in claim 9, in the presence of a metal alkoxide.

11. A process for preparing a diester of the formula:

wherein R is a $C_1$–$C_6$ alkyl, which comprises reacting an acetylene derivative of the formula:

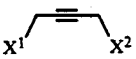

wherein $X^1$ and $X^2$ are each chlorine atom, bromine atom, iodine atom, methanesulfonyloxy, or p-toluenesulfonyloxy, with an acetoacetic acid ester of the formula:

wherein R is as defined above, in the presence of a metal alkoxide.

* * * * *